(12) United States Patent
Jenson et al.

(10) Patent No.: US 7,780,630 B2
(45) Date of Patent: Aug. 24, 2010

(54) PERFUSION DEVICE

(75) Inventors: Mark L. Jenson, Greenfield, MN (US); William J. Drasler, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 17 days.

(21) Appl. No.: 11/693,795

(22) Filed: Mar. 30, 2007

(65) Prior Publication Data
US 2008/0243072 A1 Oct. 2, 2008

(51) Int. Cl.
*A61M 31/00* (2006.01)
*A61M 37/00* (2006.01)

(52) U.S. Cl. .................. 604/103.14; 604/103.04; 604/103.06; 604/103.11; 604/103.13

(58) Field of Classification Search ........... 604/96.01, 604/103, 103.04–103.08, 103.11–103.14, 604/104, 164.05; 606/192, 194
See application file for complete search history.

(56) References Cited

U.S. PATENT DOCUMENTS

| | | | |
|---|---|---|---|
| 4,406,656 A | 9/1983 | Hattler et al. | |
| 4,425,908 A | 1/1984 | Simon | |
| 4,601,713 A | 7/1986 | Fuqua | |
| 4,710,181 A | 12/1987 | Fuqua | |
| 4,738,666 A | 4/1988 | Fuqua | |
| 5,106,368 A | 4/1992 | Uldall et al. | |
| 5,421,832 A | 6/1995 | Lefebvre | |
| 5,472,418 A | 12/1995 | Palestrant | |
| 5,474,537 A | 12/1995 | Solar | |
| 5,573,508 A | 11/1996 | Thornton | |
| 5,735,831 A | 4/1998 | Johnson et al. | |
| 5,738,667 A | 4/1998 | Solar | |
| 5,795,322 A | 8/1998 | Boudewijn | |
| 5,810,874 A | 9/1998 | Lefebvre | |
| 5,814,064 A | 9/1998 | Daniel et al. | |
| 5,827,324 A | 10/1998 | Cassell et al. | |
| 5,925,301 A * | 7/1999 | Johnson et al. | ............. 264/248 |
| 5,947,995 A | 9/1999 | Samuels | |
| 6,001,118 A | 12/1999 | Daniel et al. | |
| 6,129,739 A | 10/2000 | Khosravi | |
| 6,152,946 A | 11/2000 | Broome et al. | |
| 6,168,579 B1 | 1/2001 | Tsugita | |
| 6,179,859 B1 | 1/2001 | Bates et al. | |

(Continued)

FOREIGN PATENT DOCUMENTS

WO 03/090834 A2 11/2003

(Continued)

*Primary Examiner*—Kevin C Sirmons
*Assistant Examiner*—Bhisma Mehta
(74) *Attorney, Agent, or Firm*—Crompton, Seager & Tufte, LLC

(57) ABSTRACT

A perfusion guidewire is disclosed. The perfusion guidewire includes an elongate core member and a collapsible sheath tightly wrapped around at least the distal portion of the elongate core member such that the wrapped sheath is folded upon itself, forming a plurality of layers of material in a radial direction from the longitudinal axis of the elongate core member. The wrapped sheath is tightly wrapped about the elongate core member such that the wrapped sheath and elongate core member travel as a unit during navigation within the blood vessel of the body of a patient. The wrapped sheath is expandable to a larger diameter in order to allow a perfusate to pass through the lumen of the sheath.

15 Claims, 27 Drawing Sheets

U.S. PATENT DOCUMENTS

| | | | |
|---|---|---|---|
| 6,179,861 B1 | 1/2001 | Khosravi et al. |
| 6,183,492 B1 | 2/2001 | Hart et al. |
| 6,190,357 B1 | 2/2001 | Ferrari et al. |
| 6,245,087 B1 | 6/2001 | Addis |
| 6,277,138 B1 | 8/2001 | Levinson et al. |
| 6,277,139 B1 | 8/2001 | Levinson et al. |
| 6,290,710 B1 | 9/2001 | Cryer et al. |
| 6,336,934 B1 | 1/2002 | Gilson et al. |
| 6,361,545 B1 | 3/2002 | Macoviak et al. |
| 6,371,971 B1 | 4/2002 | Tsugita et al. |
| 6,395,014 B1 | 5/2002 | Macoviak et al. |
| 6,398,756 B2 | 6/2002 | Peterson et al. |
| 6,425,909 B1 | 7/2002 | Dieck et al. |
| 6,527,746 B1 | 3/2003 | Oslund et al. |
| 6,530,939 B1 | 3/2003 | Hopkins et al. |
| 6,537,294 B1 | 3/2003 | Boyle et al. |
| 6,544,279 B1 | 4/2003 | Hopkins et al. |
| 6,589,263 B1 | 7/2003 | Hopkins et al. |
| 6,595,967 B2 | 7/2003 | Kramer |
| 6,605,074 B2 | 8/2003 | Zadno-Azizi et al. |
| 6,645,224 B2 | 11/2003 | Gilson et al. |
| 6,740,061 B1 | 5/2004 | Oslund et al. |
| 6,936,059 B2 | 8/2005 | Belef |
| 6,939,361 B1 | 9/2005 | Kleshinski |
| 6,951,555 B1 | 10/2005 | Suresh et al. |
| 6,969,396 B2 | 11/2005 | Krolik et al. |
| 7,014,647 B2 | 3/2006 | Brady et al. |
| 2001/0005791 A1 | 6/2001 | Ginsburg et al. |
| 2002/0095174 A1 | 7/2002 | Tsugita et al. |
| 2004/0193207 A1 | 9/2004 | Boismier |
| 2004/0249409 A1 | 12/2004 | Krolik et al. |
| 2005/0101987 A1 | 5/2005 | Salahieh |
| 2005/0131449 A1 | 6/2005 | Salahieh |
| 2005/0288631 A1 | 12/2005 | Lewis et al. |
| 2006/0195138 A1 | 8/2006 | Goll et al. |

FOREIGN PATENT DOCUMENTS

| | | |
|---|---|---|
| WO | 2005/056099 A2 | 6/2005 |

* cited by examiner

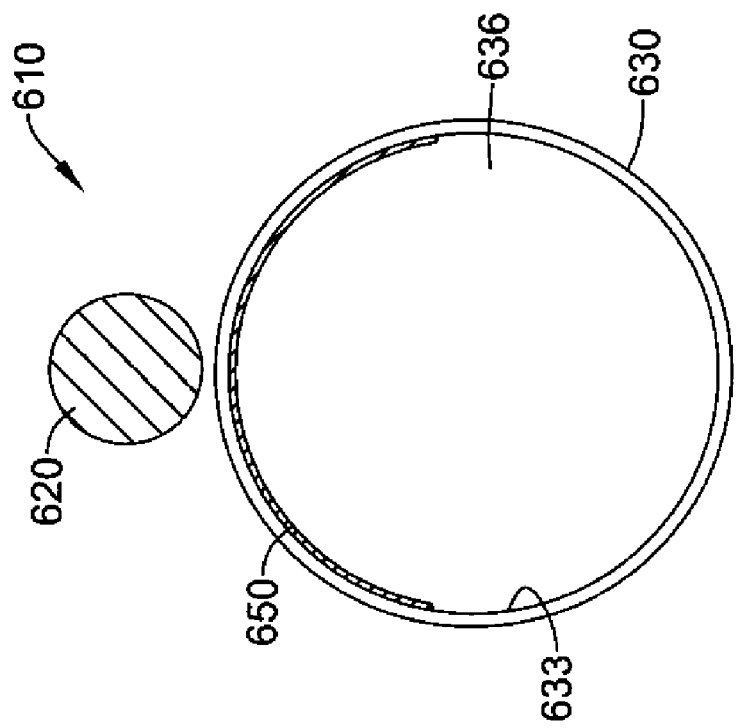
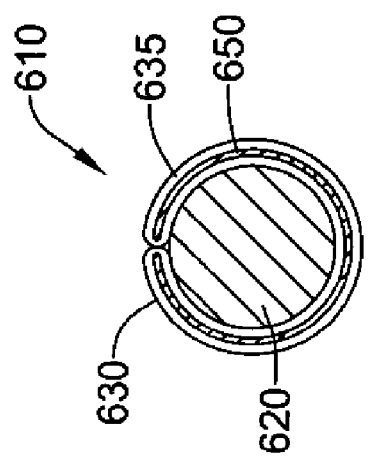
Figure 8A
Figure 8B

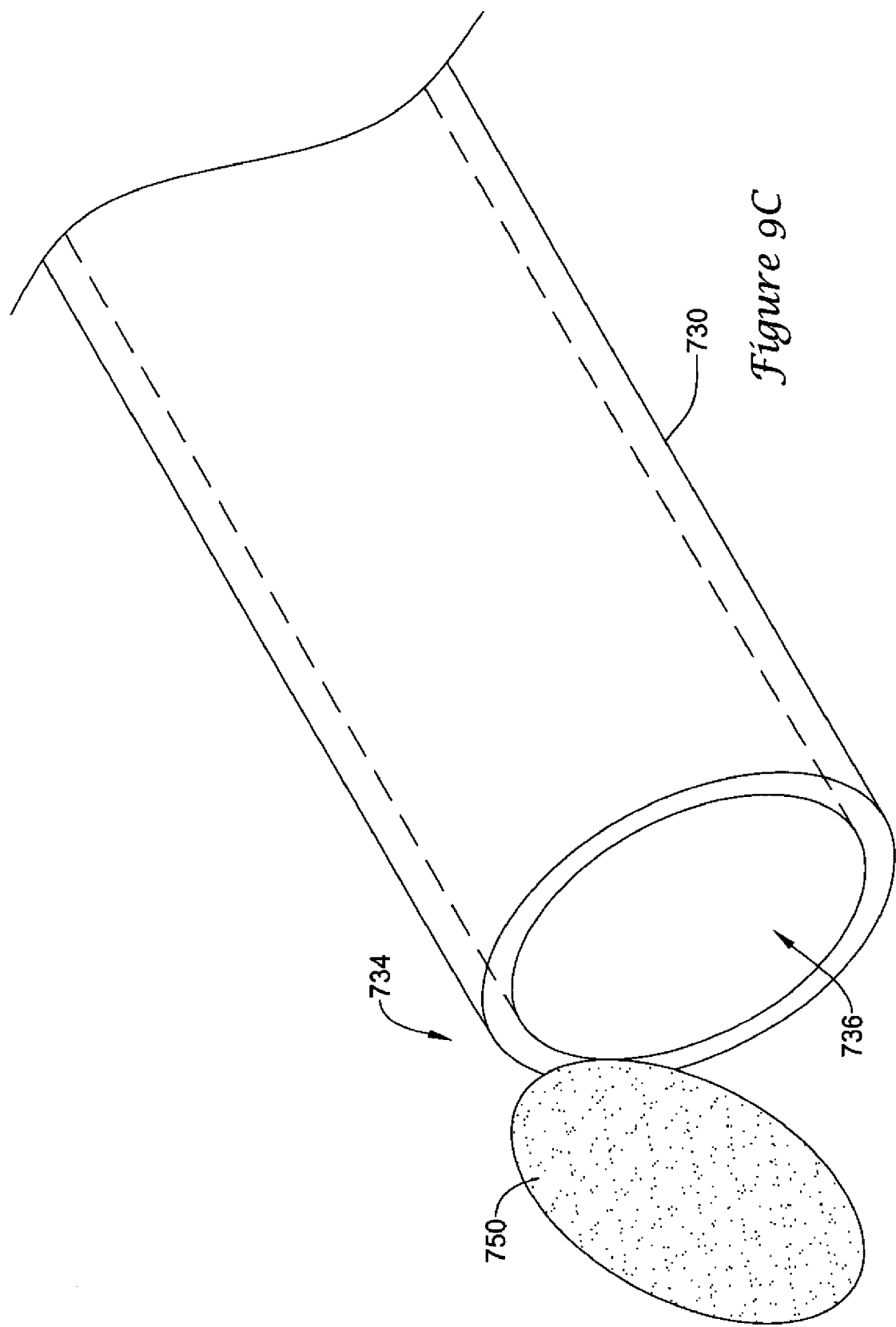

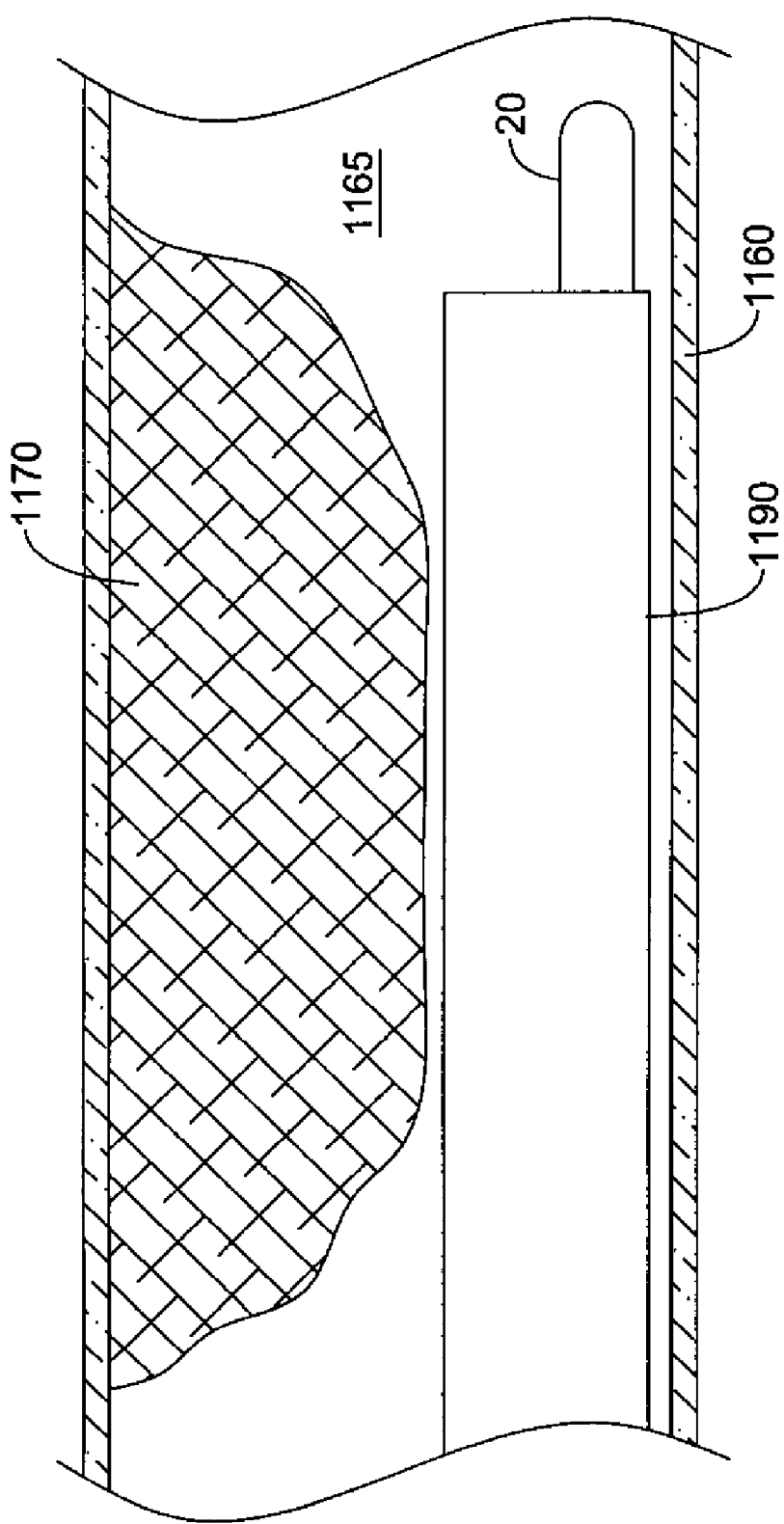

PERFUSION DEVICE

CROSS REFERENCE TO RELATED APPLICATIONS

This application is related to U.S. application Ser. No. 11/693,956, filed on Mar. 30, 2007 and entitled "PERFUSION AND EMBOLIC PROTECTION", the disclosure of which is incorporated herein by reference in its entirety.

TECHNICAL FIELD

The invention generally relates to medical devices, and more particularly pertains to apparatus, assemblies and methods of perfusing a perfusate within a blood vessel of the body of a patient.

BACKGROUND

A thrombus is a blood clot formed in a blood vessel which may cause an obstruction to blood flow. A thromboembolus is a thrombus which has disassociated from a vessel wall and migrated through the blood stream to a downstream location. A thromboembolus may become lodged in a smaller blood vessel, causing an obstruction to blood flow. A partial or complete occlusion of a blood vessel, resultant of a thrombus or thromboembolus may significantly reduce arterial blood flow, causing oxygen deprivation in tissue, called ischemia. Oxygen deprivation may lead to cell death and/or organ dysfunction. Vital organs, such as the brain, require a continuous supply of oxygen delivered by the blood in order to function properly. Significant oxygen deprivation to the brain, called a stroke, may cause permanent brain damage or even death. Therefore, at the onset of oxygen deprivation to an organ, such as the brain, caused by an occlusion, it is vital to re-establish adequate blood flow as soon as possible in order to restore the supply of oxygen to the organ.

Although medical devices exist which provide perfusion past occlusions in the vasculature, these devices are inadequate for reaching remote regions of the vasculature. Remote regions of the vasculature, such as the intracerebral arteries, are noted as being tortuous and small in lumen size. Thus, accessibility to such remote locations is dictated by the size and flexibility characteristics of the medical device used to reach such remote locations. Additionally, attempting to cross an occlusion with a device of considerable size may be inhibitive and/or may dislodge the occlusion, adding further risks to treatment procedures. Therefore, a need remains for an improved apparatus, assembly and/or method for crossing and/or for re-establishing blood flow past an occlusion, such as a thrombus or a thromboembolus, in a blood vessel of the body of a patient.

SUMMARY

The disclosure is directed to a perfusion guidewire for use in crossing an occlusion within a blood vessel of the body of a patient in order to establish flow of a perfusate distal of the occlusion.

Accordingly, one illustrative embodiment is a perfusion guidewire including an elongate core member and a collapsible sheath tightly wrapped around at least the distal portion of the elongate core member such that the wrapped sheath is folded upon itself, forming a plurality of layers of material in a radial direction from the longitudinal axis of the elongate core member. The wrapped sheath is tightly wrapped about the elongate core member such that the wrapped sheath and elongate core member travel as a unit during navigation within the blood vessel of the body of a patient. The wrapped sheath is expandable to a larger diameter in order to allow a perfusate to pass through the lumen of the sheath.

Another illustrative embodiment is a method of perfusing a perfusate past an occlusion in a blood vessel of the body of a patient. The method includes providing a guidewire including an elongate core member and a sheath folded around at least a portion of the elongate core member. With the sheath folded around the elongate core member, the guidewire may be advanced through the blood vessel such that the distal end of the sheath is advanced distal of the occlusion while the proximal end of the sheath remains external of the body of the patient. The folded sheath is expanded and a perfusate may be perfused through the sheath from a source external of the body of the patient to a location distal of the occlusion.

BRIEF DESCRIPTION OF THE DRAWINGS

The invention may be more completely understood in consideration of the following detailed description of various embodiments in connection with the accompanying drawings, in which:

FIGS. 8A and 8B are cross-sectional views illustrating an alternative arrangement of expanding a sheath of a perfusion guidewire;

FIGS. 9A-9C illustrate an alternative arrangement of using a seal in the form of a flap in order to expand the sheath of a perfusion guidewire;

FIGS. 13A-13F illustrate an exemplary method of using the illustrative perfusion guidewire of FIG. 1 in a medical procedure;

Figure 1:
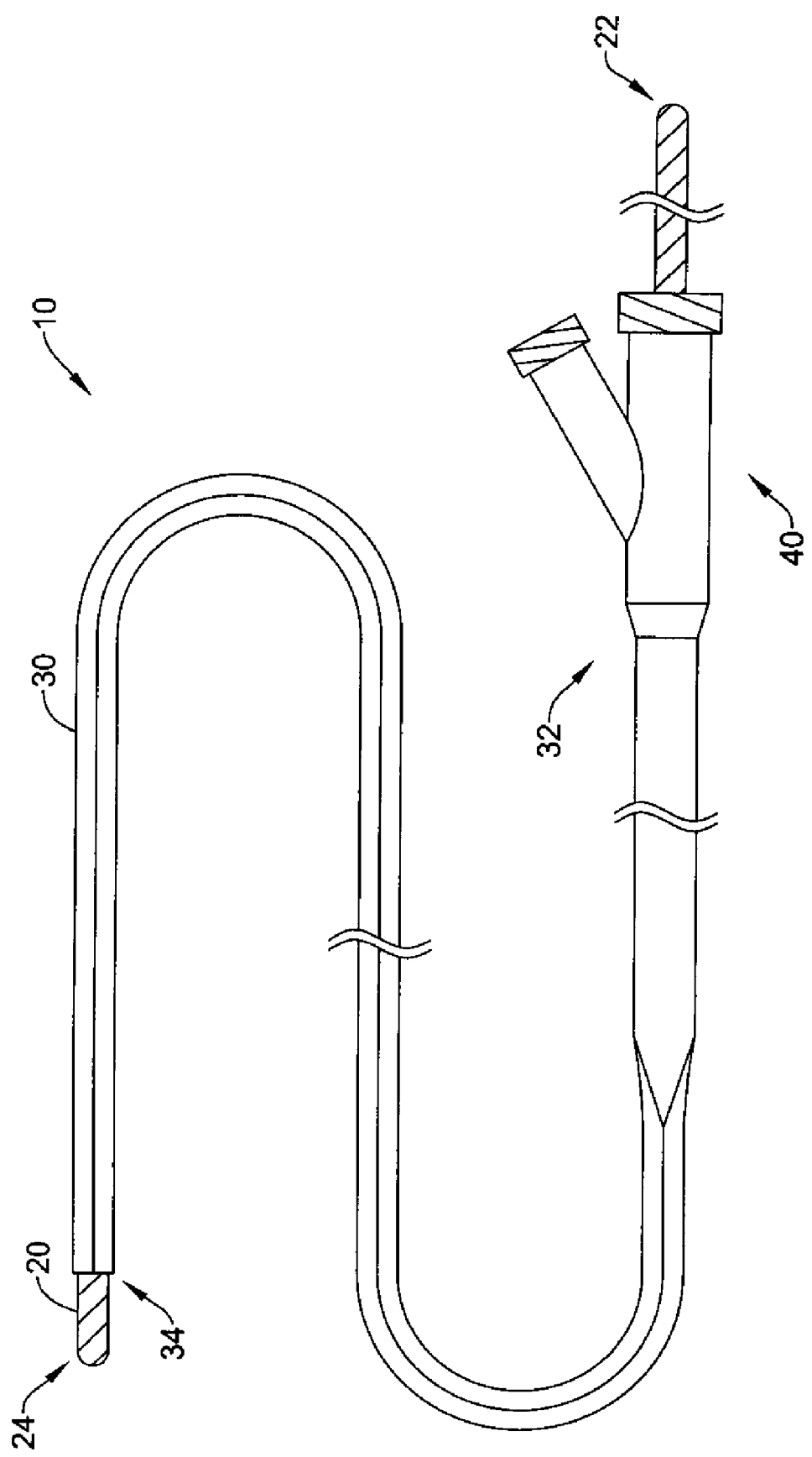
FIG. 1 illustrates an exemplary embodiment of a perfusion guidewire.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to FIG. 1, an exemplary perfusion device is generally shown. The perfusion guidewire 10 includes an elongate core member 20 and a sheath 30 wrapped about the elongate core member 20. The arrangement of the elongate core member 20 and the sheath 30 may be considered a pseudo-OTW (over-the-wire) device, as substantially the entire length of the sheath 30 may be wrapped about the elongate core member 20, thus surrounded by the sheath 30. The elongate core member 20 and the sheath 30, two components of the perfusion guidewire 10, are united together such that they travel as a unit during navigation within the blood vessel of the body of the patient. In the collapsed configuration, the sheath 30 may be releasably secured to the elongate core member 20 such that longitudinal movement of the elongate core member 20 corresponds to equivalent longitudinal movement of the sheath 30. The elongate core member 20 may provide the perfusion guidewire 10 with sufficient column strength and rigidity during introduction within the vasculature not attainable with the sheath 30 or guidewire 10 alone.

The elongate core member 20 has a proximal end 22 and a distal end 24. In some embodiments, the length of the elongate core member 20 may be about 50 cm to about 300 cm, about 150 cm to about 300 cm, or about 100 cm to about 200 cm. In some embodiments, the diameter of the core member 20 may be about 0.25 mm to about 0.5 mm (about 0.01 inches to about 0.02 inches) or about 0.355 mm to about 0.457 mm (about 0.014 inches to about 0.018 inches). However, in other embodiments, the diameter of the elongate core member 20 may be less than 0.25 mm (0.01 inches). Although some suitable dimensions are disclosed, one of skill in the art, incited by the present disclosure, would understand that desired dimensions may deviate from those expressly disclosed herein.

The sheath 30 has a proximal end 32, a distal end 34 and a lumen 36 (shown in FIG. 3B) extending therethrough. In some embodiments, the length of the sheath 30 may be greater than 50 cm, greater than 100 cm, greater than 150 cm, or greater than 200 cm. Thus, in some embodiments, the sheath 30 may extend a majority of, a substantial portion of, or substantially the entire length of the elongate core member 20. Although some suitable dimensions are disclosed, one of skill in the art, incited by the present disclosure, would understand that desired dimensions may deviate from those expressly disclosed herein. The sheath 30 is sized such that a proximal portion of the sheath 30 may remain exterior to the body of a patient during a perfusion procedure. Therefore, a connector 40, which may include one or more luer fittings, may be attached to the proximal end 32 of the sheath 30 exterior of the body of a patient such that the sheath 30 may be coupled to another medical device, such as a pumping apparatus (not shown) providing a flow of pressurized perfusate to the lumen 36 during a medical procedure.

In some embodiments, such as that illustrated in FIG. 1, a proximal portion of the sheath 30 may be annular in shape when the sheath 30 is in the collapsed, folded configuration. In other words, the proximal portion of the sheath 30 may retain an annular shape while the distal portion of the sheath 30 is folded and wrapped around the circumference of the elongate core member 20. In some embodiments, the proximal portion of the sheath 30 may have sufficient rigidity such that the proximal portion may not be readily folded and collapsed.

Figure 2:
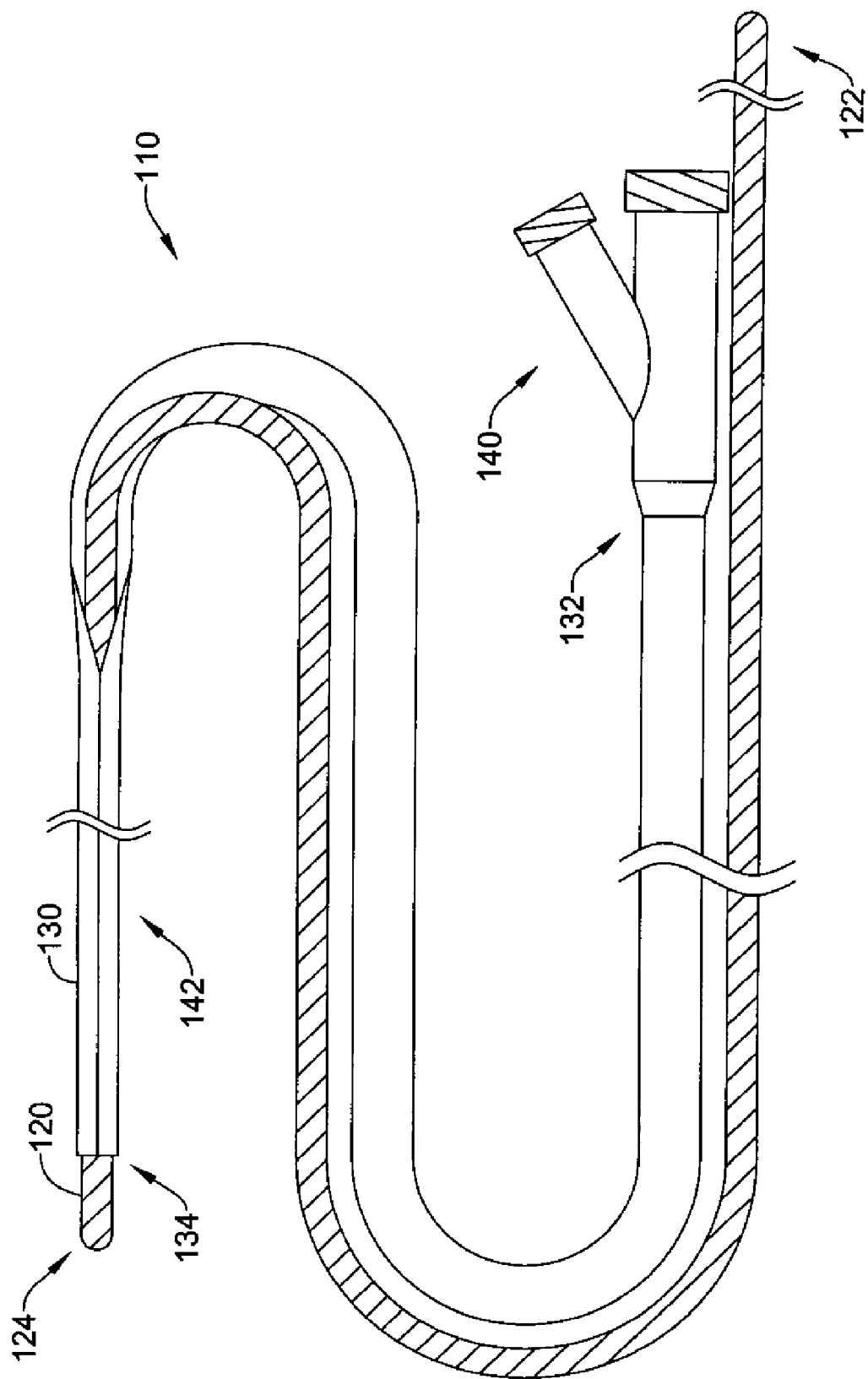
FIG. 2 illustrates another exemplary embodiment of a perfusion guidewire.

Another exemplary perfusion device is generally shown in FIG. 2. The perfusion guidewire 110 includes an elongate core member 120 and a sheath 130 wrapped about a distal portion 142 of the elongate core member 120. The arrangement of the elongate core member 120 and the sheath 130 may be considered a pseudo-RX (rapid exchange) device, as only the distal portion 142 of the elongate core member 120 is surrounded by the sheath 130. As such, a proximal portion, which may be a majority or a substantial portion of the length of the elongate core member 120, is positioned exterior of the sheath 130 such that the proximal portion of the elongate core member 120 extends generally parallel to and alongside the sheath 130. The proximal portion of the elongate core member 120 may be generally spaced from an exterior surface of the sheath. The elongate core member 120 and the sheath 130, two components of the perfusion guidewire 110, are united together such that they travel as a unit during navigation within the blood vessel of the body of the patient. In the collapsed configuration, the sheath 130 may be releasably secured to the elongate core member 120 such that longitudinal movement of the elongate core member 120 corresponds to equivalent longitudinal movement of the sheath 130. The elongate core member 120 may provide the perfusion guidewire 110 with sufficient column strength and rigidity during introduction within the vasculature not attainable with the sheath 130 or guidewire 110 alone.

The elongate core member 120 has a proximal end 122 and a distal end 124. In some embodiments, the length of the elongate core member 120 may be about 50 cm to about 300 cm, about 150 cm to about 300 cm, or about 100 cm to about 200 cm. In some embodiments, the diameter of the core member 120 may be about 0.25 mm to about 0.5 mm (about 0.01 inches to about 0.02 inches) or about 0.355 mm to about 0.457 mm (about 0.014 inches to about 0.018 inches). However, in other embodiments, the diameter of the elongate core member 120 may be less than 0.25 mm (0.01 inches). Although some suitable dimensions are disclosed, one of skill in the art, incited by the present disclosure, would understand that desired dimensions may deviate from those expressly disclosed herein.

The sheath 130 has a proximal end 132, a distal end 134 and a lumen 136 (shown in FIG. 4B) extending therethrough. In some embodiments, the length of the sheath 130 may be greater than 50 cm, greater than 100 cm, greater than 150 cm, or greater than 200 cm. Thus, in some embodiments, the sheath 130 may extend a majority of, a substantial portion of, or substantially the entire length of the elongate core member 120. Although some suitable dimensions are disclosed, one of skill in the art, incited by the present disclosure, would understand that desired dimensions may deviate from those expressly disclosed herein. The sheath 130 is sized such that a proximal portion of the sheath 130 may remain exterior to the body of a patient during a perfusion procedure. Therefore, a connector 140, which may include one or more luer fittings, may be attached to the proximal end 132 of the sheath 130 exterior of the body of a patient such that the sheath 130 may be coupled to another medical device, such as a pumping apparatus (not shown) providing a flow of pressurized perfusate to the lumen 136 during a medical procedure.

In some embodiments, such as that illustrated in FIG. 2, a proximal portion of the sheath 130 may be annular in shape when the sheath 130 is in the collapsed, folded configuration. In other words, the proximal portion of the sheath 130 may retain an annular shape while the distal portion of the sheath 130 is folded and wrapped around the circumference of the elongate core member 120. In some embodiments, the proximal portion of the sheath 130 may have sufficient rigidity such that the proximal portion may not be readily folded and collapsed.

Figure 3:
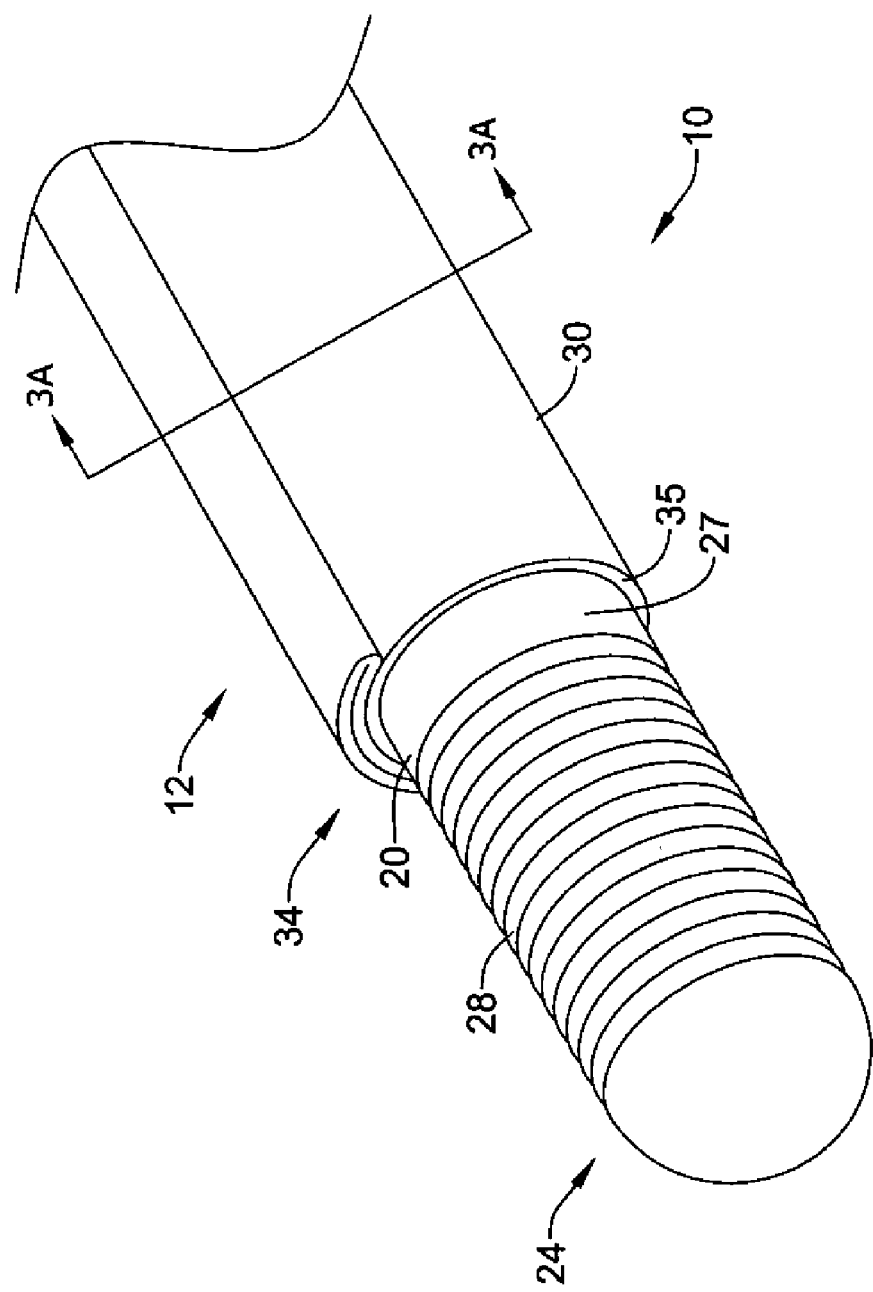
FIG. 3 is a perspective view of the distal portion of the perfusion guidewire of FIG. 1.

The distal portion 12 of the perfusion guidewire 10 of FIG. 1 is illustrated in FIG. 3. As shown in FIG. 3, in some embodiments the elongate core member 20 may include a spring tip 28 proximate the distal end 24 of the elongate core member 20. However, in other embodiments the elongate core member 20 may include another style of atraumatic and/or flexible tip known in the art. In some embodiments, the distal end 34 of the sheath 30 may be positioned about 1 cm to about 10 cm, about 1 cm to about 5 cm, or about 1 cm to about 3 cm proximal of the distal end 24 of the elongate core member 20.

The elongate core member 20 may be a solid member having a solid cross-section, or the elongate core member 20 may be a hollow member having an annular cross-section in some embodiments. The elongate core member 20 may be formed of any suitable material such as a metallic material or a polymeric material, or a combination of metallic and polymeric materials. Some suitable metallic materials include, but are not necessarily limited to, stainless steel, tungsten, nickel-titanium alloys such as those possessing shape memory properties commonly referred to as nitinol, nickel-chromium alloys, nickel-chromium-iron alloys, or other suitable metals, or combinations or alloys thereof. Some suitable polymeric materials include, but are not necessarily limited to, polyamide, polyether block amide, polyethylene, polyethylene terephthalate, polypropylene, polyvinylchloride, polyurethane, polytetrafluoroethylene, and copolymers, blends, mixtures or combinations thereof.

The sheath 30, in a collapsed configuration, may be wrapped about the outer surface 27 of the elongate core member 20 such that the wall 35 of the sheath 30 is folded upon itself. In the folded configuration, the guidewire 10 may assume a low profile such that the guidewire 10 may be navigated to remote locations within the vasculature of a patient. In some embodiments, the distal portion 12 of the guidewire 10, including the elongate core member 20 and the sheath 30, may have an outer diameter in the collapsed configuration commensurate to that of a typical guidewire (e.g., 0.014 inches or 0.018 inches). It is noted that in some embodiments, such as that illustrated in FIG. 1, a more proximal portion of the sheath 30 of the guidewire 10 may have a larger diameter than that of the distal portion 12, as desired.

Figure 3B:
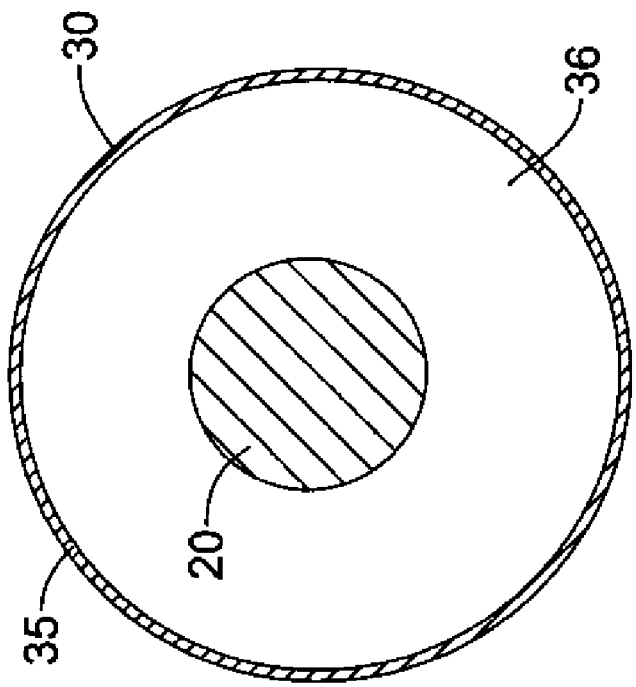
FIG. 3B is a cross-sectional view of the perfusion guidewire of FIG. 3 in an expanded state.
Figure 3A:
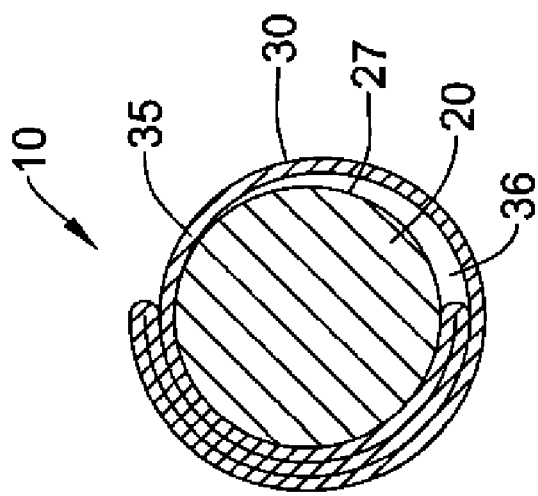
FIG. 3A is a cross-sectional view of the perfusion guidewire of FIG. 3 taken along line 3A-3A of FIG. 3.

FIG. 3A shows a cross-sectional view of the distal portion 12 of the guidewire 10 taken along Line 3A-3A of FIG. 3. As shown in FIG. 3A, the elongate core member 20 may be located within the lumen 36 of the sheath 30. The wall 35 of the sheath 30 may be tightly folded into a serpentine arrangement about the outer surface 27 of the elongate core member 20.

The wall 35 of the sheath 30, which may be considered a thin wall, may have a thickness which readily allows the sheath 30 to buckle and fold upon itself in order to collapse the lumen 36 of the sheath 30. For instance, in some embodiments the thickness of the wall 35 of the sheath 30 may be about 0.0075 mm to about 0.05 mm (about 0.0003 inches to about 0.002 inches), or about 0.0125 mm to about 0.025 mm (about 0.0005 inches to about 0.001 inches), or about 0.025 mm (about 0.001 inches). Although some suitable dimensions are disclosed, one of skill in the art, incited by the present disclosure, would understand that desired dimensions may deviate from those expressly disclosed herein. The chosen thickness of the wall 35 affords the wall 35 pliable in order to readily fold back upon itself when collapsed and wrapped around the elongate core member 20.

The sheath 30 may be formed from any desirable material. Some suitable polymeric materials include, but are not necessarily limited to, polyether block amide, polyvinylchloride, polyethylene terephthalate, poly(ethylene-co-methacrylic acid) commonly known as Surlyn® available from DuPont, polyamides, polyimides, polydimethylsiloxane, polyurethane and other silicone or other rubber materials or elastomers, polytetrafluoroethylene (PTFE) or other fluoropolymers, and copolymers, blends, mixtures or combinations thereof. In some embodiments, the material of the sheath 30 is chosen to be supple, yet generally nondistensible. In describing the material as being generally nondistensible, what is meant is that the chosen material is not able to be elastically stretched (i.e., inelastic in a radial direction) at perfusate operating pressures of 400 mmHg or less. In other embodiments, the material of the sheath 30 may be a supple, elastic material allowing the sheath 30 to be elastically stretched in a radial direction at perfusate operating pressures of 400 mmHg or less. One of ordinary skill in the art would recognize circumstances in which an elastic material would be preferred, as well as circumstances in which an inelastic material would be preferred.

In the collapsed configuration, the wall 35 of the sheath 30 may be folded upon itself, forming a plurality of layers of material in a radial direction from the longitudinal axis of the elongate core member 20. For example, as shown in FIG. 3A, in the collapsed configuration, the sheath 30 may be folded such that three layers of material are circumferentially placed radially adjacent of a contiguous layer. In the illustrative embodiment, the sheath 30 is wrapped about the elongate core member 20 a total of about 540 degrees. However, in other embodiments, the sheath 30 may be wrapped about the elongate core member 20 to other extents, for example about 360 degrees, about 450 degrees, about 630 degrees, or about 720 degrees. It is noted that in embodiments wherein the elongate core member 20 is positioned within the lumen 36 of the sheath 30, such as that illustrated in FIG. 3A, there is an odd number of folded layers of material at any given polar direction from the longitudinal axis of the elongate core member 20. For example, there may be one, three, five, or more folded layers at any given polar direction from the longitudinal axis of the elongate core member 20.

FIG. 3B illustrates the sheath 30 in an expanded configuration. As shown in FIG. 3B the elongate core member 20 extends through the lumen 36 of the sheath 30, yet is unattached to the sheath 30 in the expanded configuration. When expanded, the wall 35 of the sheath 30 may be annular in shape. In the expanded configuration, the sheath 30 may have a lumen size of about 0.75 mm to about 1.15 mm (about 0.03 inches to about 0.045 inches), in some embodiments. Sized accordingly, the sheath 30 may readily allow the flow of red blood cells (normally 4-8 μm in diameter) therethrough with minimal shearing. Additionally, the elongate core member 20 may be used as a guide, since once positioned, other devices may be tracked along the elongate core member 20 through the sheath 30 to a desired location within the vasculature of a patient.

In some embodiments, the sheath 30 may be expanded from its collapsed, wrapped configuration to its expanded configuration by pressurizing the lumen 36 of the sheath 30. For example, in some embodiments, a pressure greater than the mean arterial pressure of the patient may be used to expand the sheath 30. For instance, a pressure of about 50 mmHg or more, 100 mmHg or more, 150 mmHg or more, 200 mmHg or more, or 300 mmHg or more may be used to expand the sheath 30. However, as described herein, other means may be utilized in order to expand the sheath 30 from its collapsed, wrapped configuration.

The inner and/or outer surface of the sheath 30 may include a coating such as a hydrophobic, hydrophilic, lubricious, protective, medicinal, or any other suitable type of coating. Suitable hydrophobic coating materials may include silicone and the like. Suitable hydrophilic coatings may include high-density polyethylene, polytetrafluoroethylene, polyarylene oxide, polyvinylpyrrolidone, polyvinylalcohols, hydroxyl alkyl cellulosics, aligns, saccharides, caprolactones, and the like, as well as mixtures and combinations thereof. Hydrophilic polymers may be blended among themselves or with formulated amounts of water insoluble compounds (including some polymers) to yield coatings with suitable lubricity, bonding and solubility. Other coatings, known to those of skill in the art, may also be applied to the sheath 30, as desired.

Figure 4:
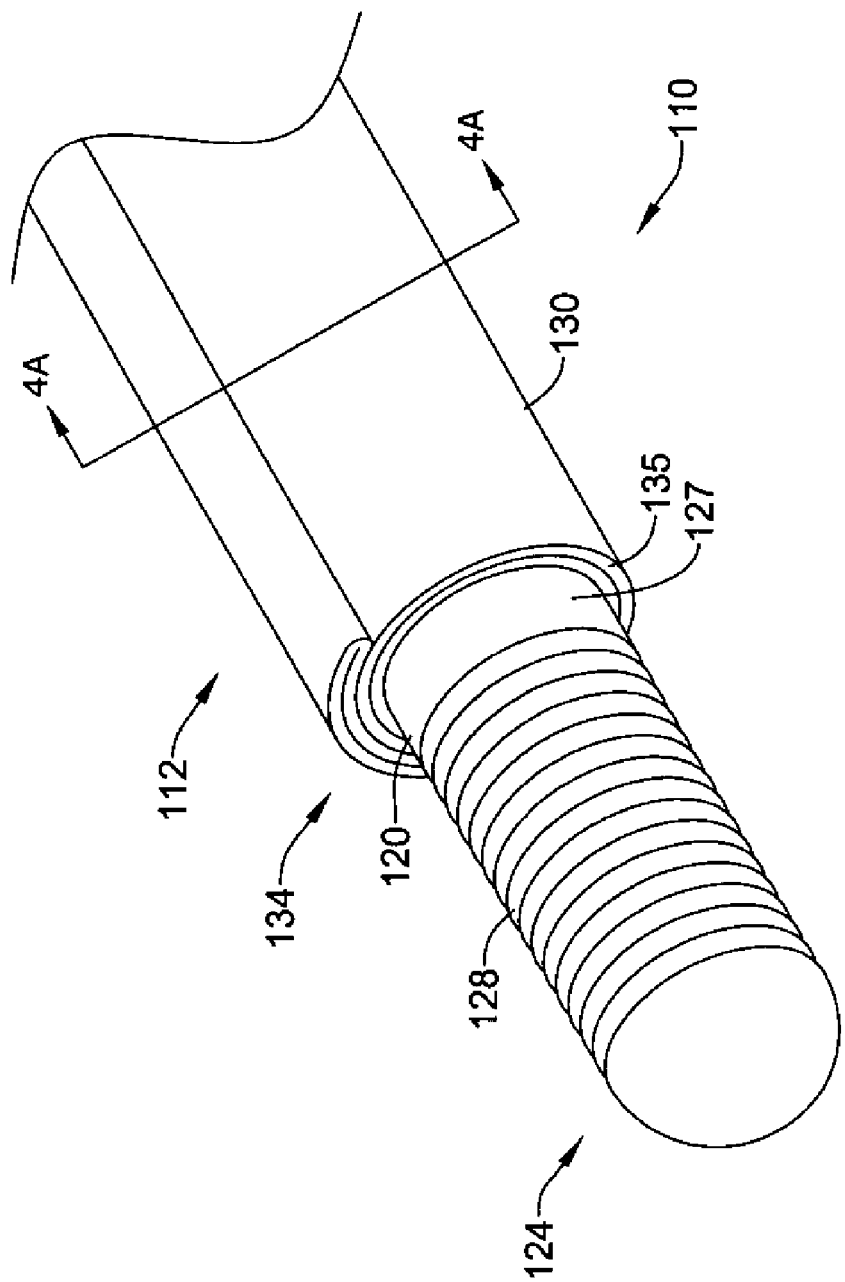
FIG. 4 is a perspective view of the distal portion of the perfusion guidewire of FIG. 2.

The distal portion 112 of the perfusion guidewire 110 of FIG. 2 is illustrated in FIG. 4. As shown in FIG. 4, in some embodiments the elongate core member 120 may include a spring tip 128 proximate the distal end 124 of the elongate core member 120. However, in other embodiments the elongate core member 120 may include another style of atraumatic and/or flexible tip known in the art. In some embodiments, the distal end 134 of the sheath 130 may be positioned about 1 cm to about 10 cm, about 1 cm to about 5 cm, or about 1 cm to about 3 cm proximal of the distal end 124 of the elongate core member 120.

The elongate core member 120 may be a solid member having a solid cross-section, or the elongate core member 120 may be a hollow member having an annular cross-section in some embodiments. The elongate core member 120 may be formed of any suitable material such as a metallic material or a polymeric material, or a combination of metallic and polymeric materials. Some suitable metallic materials include, but are not necessarily limited to, stainless steel, tungsten, nickel-titanium alloys such as those possessing shape memory properties commonly referred to as nitinol, nickel-chromium alloys, nickel-chromium-iron alloys, or other suitable metals, or combinations or alloys thereof. Some suitable polymeric materials include, but are not necessarily limited to, polyamide, polyether block amide, polyethylene, polyethylene terephthalate, polypropylene, polyvinylchloride, polyurethane, polytetrafluoroethylene, and copolymers, blends, mixtures or combinations thereof.

The sheath 130, in a collapsed configuration, may be wrapped about the outer surface 127 of the elongate core member 120 such that the wall 135 of the sheath 130 is folded upon itself. In the folded configuration, the guidewire 110 may assume a low profile such that the guidewire 110 may be navigated to remote locations within the vasculature of a patient. In some embodiments, the distal portion 112 of the guidewire 110, including the elongate core member 120 and the sheath 130, may have an outer diameter in the collapsed configuration commensurate to that of a typical guidewire (e.g., 0.014 inches or 0.018 inches). It is noted that in some embodiments, such as that illustrated in FIG. 2, a more proximal portion of the sheath 130 of the guidewire 110 may have a larger diameter than that of the distal portion 112, as desired.

Figure 4B:
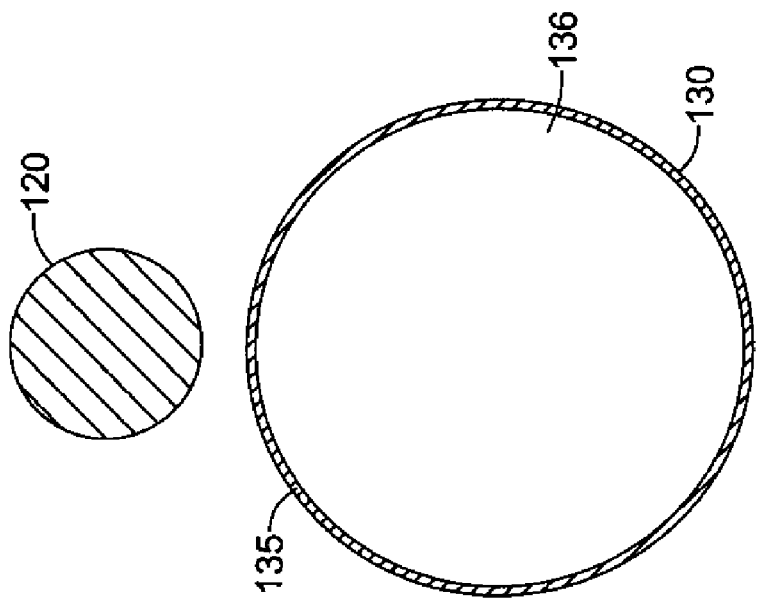
FIG. 4B is a cross-sectional view of the perfusion guidewire of FIG. 4 in an expanded state.
Figure 4A:
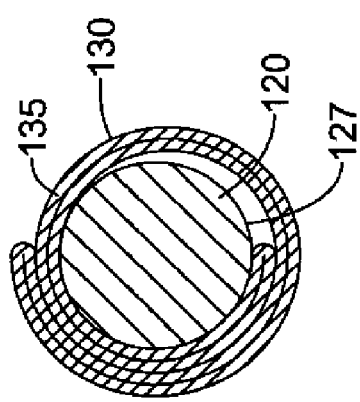
FIG. 4A is a cross-sectional view of the perfusion guidewire of FIG. 4 taken along line 4A-4A of FIG. 4.

FIG. 4A shows a cross-sectional view of the distal portion 112 of the guidewire 110 taken along Line 4A-4A of FIG. 4. As shown in FIG. 4A, the elongate core member 120 may be located exterior of the lumen 136 of the sheath 130. The wall 135 of the sheath 130 may be tightly folded into a serpentine arrangement about the outer surface 127 of the elongate core member 120.

Although, in some embodiments such as that depicted in FIG. 2, only the distal portion of the sheath 130 is wrapped about the elongate core member 120, in other embodiments, substantially the entire length of the sheath 130 may be wrapped about the elongate core member 120.

The wall 135 of the sheath 130, which may be considered a thin wall, may have a thickness which readily allows the sheath 130 to buckle and fold upon itself in order to collapse the lumen 136 of the sheath 130. For instance, in some embodiments the thickness of the wall 135 of the sheath 130 may be about 0.0075 mm to about 0.05 mm (about 0.0003 inches to about 0.002 inches), or about 0.0125 mm to about 0.025 mm (about 0.0005 inches to about 0.001 inches), or about 0.025 mm (about 0.001 inches). Although some suitable dimensions are disclosed, one of skill in the art, incited by the present disclosure, would understand that desired dimensions may deviate from those expressly disclosed herein. The chosen thickness of the wall 135 affords the wall 135 pliable in order to readily fold back upon itself when collapsed and wrapped around the elongate core member 120.

The sheath 130 may be formed from any desirable material. Some suitable polymeric materials include, but are not necessarily limited to, polyether block amide, polyvinylchloride, polyethylene terephthalate, poly(ethylene-co-methacrylic acid) commonly known as Surlyn® available from DuPont, polyamides, polyimides, polydimethylsiloxane, polyurethane and other silicone or other rubber materials or elastomers, polytetrafluoroethylene (PTFE) or other fluoropolymers, and copolymers, blends, mixtures or combinations thereof. In some embodiments, the material of the sheath 130 is chosen to be supple, yet generally nondistensible. In describing the material as being generally nondistensible, what is meant is that the chosen material is not able to be elastically stretched (i.e., inelastic in a radial direction) at perfusate operating pressures of 400 mmHg or less. In other embodiments, the material of the sheath 130 may be a supple, elastic material allowing the sheath 130 to be elastically stretched in a radial direction at perfusate operating pressures of 400 mmHg or less. One of ordinary skill in the art would recognize circumstances in which an elastic material would be preferred, as well as circumstances in which an inelastic material would be preferred.

In the collapsed configuration, the wall 135 of the sheath 130 may be folded upon itself, forming a plurality of layers of material in a radial direction from the longitudinal axis of the elongate core member 120. For example, as shown in FIG. 4A, in the collapsed configuration, the sheath 130 may be folded such that two or four layers of material are circumferentially placed radially adjacent of a contiguous layer. In the illustrative embodiment, the sheath 130 is wrapped about the elongate core member 120 a total of about 540 degrees. However, in other embodiments, the sheath 130 may be wrapped about the elongate core member 120 to other extents, for example, about 360 degrees, about 450 degrees, about 630 degrees, or about 720 degrees. It is noted that in embodiments wherein the elongate core member 120 is positioned exterior of the lumen 136 of the sheath 130, such as that illustrated in FIG. 4A, there is an even number of folded layers of material at any given polar direction from the longitudinal axis of the elongate core member 120. For example, there may be two, four, six, or more folded layers at any given polar direction from the longitudinal axis of the elongate core member 120.

FIG. 4B illustrates the sheath 130 in an expanded configuration. As shown in FIG. 4B the elongate core member 120 extends alongside and generally parallel with the sheath 130, exterior of the lumen 136 of the sheath 130, in the expanded configuration. In some embodiments, when expanded, the outer surface of the elongate core member 120 may be generally spaced from the outer of surface of the sheath. In the illustrated embodiment, the elongate core member 120 is unattached to the sheath 130. When expanded, the wall 135 of the sheath 130 may be annular in shape. In the expanded configuration, the sheath 130 may have a lumen size of about 0.75 mm to about 1.15 mm (about 0.03 inches to about 0.045 inches), in some embodiments. Sized accordingly, the sheath 130 may readily allow the flow of red blood cells (normally 4-8 μm in diameter) therethrough with minimal shearing. Additionally, the elongate core member 120 may be used as a guide, since once positioned, other devices may be tracked along the elongate core member 120 alongside the sheath 130 to a desired location within the vasculature of a patient.

In some embodiments the sheath 130 may be expanded from its collapsed, wrapped configuration to its expanded configuration by pressurizing the lumen 136 of the sheath 130. For example, in some embodiments, a pressure greater than the mean arterial pressure of the patient may be used to expand the sheath 130. For instance, a pressure of about 50 mmHg or more, 100 mmHg or more, 150 mmHg or more, 200 mmHg or more, or 300 mmHg or more may be used to expand the sheath 130. However, as described herein, other means may be utilized in order to expand the sheath 130 from its collapsed, wrapped configuration.

The inner and/or outer surface of the sheath 130 may include a coating such as a hydrophobic, hydrophilic, lubricious, protective, medicinal, or any other suitable type of coating. Suitable hydrophobic coating materials may include silicone and the like. Suitable hydrophilic coatings may include high-density polyethylene, polytetrafluoroethylene, polyarylene oxide, polyvinylpyrrolidone, polyvinylalcohols, hydroxyl alkyl cellulosics, aligns, saccharides, caprolactones, and the like, as well as mixtures and combinations thereof. Hydrophilic polymers may be blended among themselves or with formulated amounts of water insoluble compounds (including some polymers) to yield coatings with suitable lubricity, bonding and solubility. Other coatings, known to those of skill in the art, may also be applied to the sheath 130, as desired.

Figure 5B:
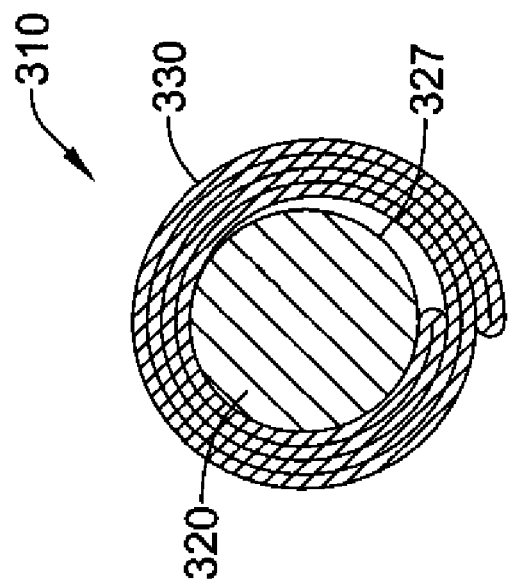
FIG. 5B is a cross-sectional view of an alternative embodiment of a perfusion guidewire.
Figure 5A:
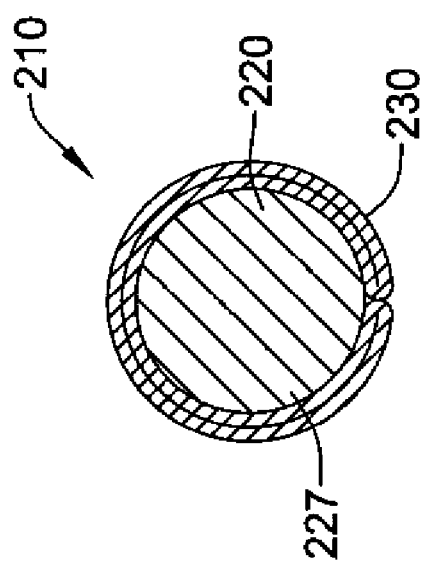
FIG. 5A is a cross-sectional view of an alternative embodiment of a perfusion guidewire.

FIGS. 5A and 5B are cross-sectional views taken of alternative embodiments of perfusion guidewires. The perfusion guidewire 210, shown in FIG. 5A, includes an elongate core member 220 and a sheath 230 wrapped about the outer surface 227 of the elongate core member 220. In the illustrative embodiment, the sheath 230 is wrapped 360 degrees around the circumference of the elongate core member 220. The perfusion guidewire 310, shown in FIG. 5B, includes an elongate core member 320 and a sheath 330 wrapped about the outer surface 327 of the elongate core member 320. In the illustrative embodiment, the sheath 330 is wrapped 720 degrees around the circumference of the elongate core member 330. In other embodiments, the sheath of the perfusion guidewire may be wrapped around the circumference of the elongate core member any desired amount. For example, the sheath may be wrapped about 360 degrees, about 450 degrees, about 540 degrees, about 630 degrees, about 720 degrees, or more around the circumference of the elongate core member. It is noted, that the extent of wraps of the sheath dictates how many layers of material are at any given polar direction from the longitudinal axis of the elongate core member. Additionally, as noted above, depending on whether the elongate core member is positioned within the lumen of the sheath or exterior of the sheath, there may be a plurality, either an odd number or an even number, of folded layers of at any given polar direction from the longitudinal axis of the elongate core member.

Figure 6:
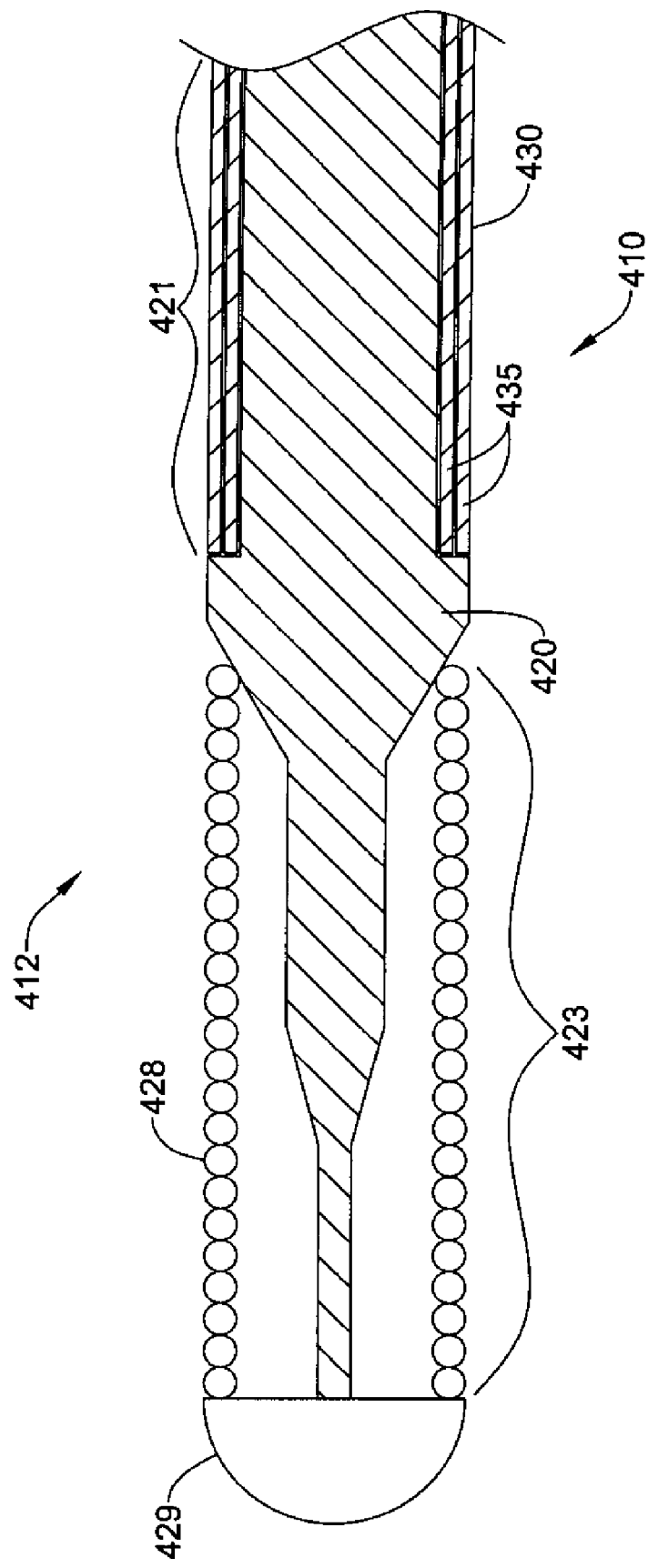
FIG. 6 is a cross-sectional view of the distal portion of an alternative embodiment of a perfusion guidewire.

A cross-sectional view of an alternative embodiment of a distal portion 412 of a perfusion guidewire 410 is illustrated in FIG. 6. The elongate core member 420 includes a spring tip 428 surrounding a tapered distal portion 423 of the elongate core member 420. A solder ball 429 may be used to secure the spring tip 428 to the distal end of the elongate core member 420. A reduced diameter region 421 of the elongate core member 420 may be located proximal of the distal end of the elongate core member 420. The reduced diameter region 421 may have a diameter less than the diameter of a more distal portion of the elongate core member 420. In some embodiments, the elongate core member 420 may be centerless ground in order to form the reduced diameter region 421. However, one of skill in the art would understand alternative methods of forming the reduced diameter region 421 in the elongate core member 420.

The sheath 430 may be positioned and wrapped around the circumference of the reduced diameter region 421 in order to reduce the overall profile of the distal portion 412 of the guidewire 410. For instance, in some embodiments, the elongate core member 420 may generally have a diameter of 0.014 inches and a reduced diameter region 421 having a diameter of 0.01 inches. Thus, a sheath 430, having a wall thickness of 0.001 inches, may be wrapped about the reduced diameter region 421. In the illustrative embodiment, the sheath 430 includes two folded layers 435 of at any given polar direction from the longitudinal axis of the elongate core member 420. Thus, the overall profile of the distal portion 412 of the guidewire 410 may be maintained at a diameter of 0.014 inches. Alternatively, the elongate core member 420 may generally have a diameter of 0.018 inches and a reduced diameter region 421 having a diameter of 0.014 inches. Thus, the overall profile of the distal portion 412 of the guidewire 410 may be maintained at a diameter of 0.018 inches when a sheath 430, including two folded layers 435 (having a wall thickness of 0.001 inches), is wrapped around the circumference of the reduced diameter region 421. Although some suitable dimensions are disclosed, one of skill in the art, incited by the present disclosure, would understand that desired dimensions may deviate from those expressly disclosed herein.

Figure 7:
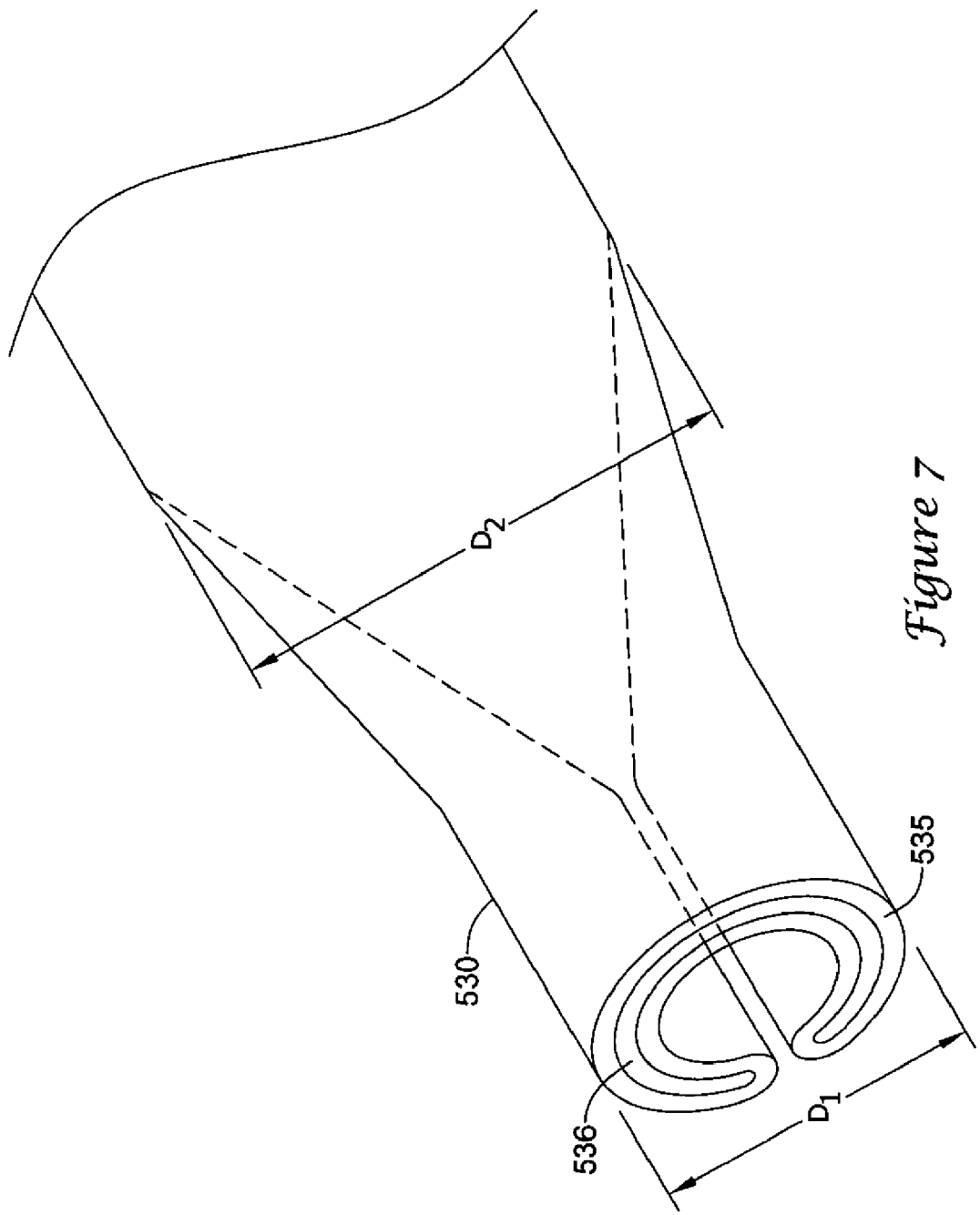
FIG. 7 is a perspective view of a sheath of a perfusion guidewire at a transitional stage during expansion or unfolding of the sheath.

A sheath 530 is shown in FIG. 7 at a transitional stage during expansion or unfolding of the sheath 530. It is noted that the elongate core member is not illustrated in FIG. 7 for purposes of clarity. Although FIG. 7 illustrates gaps defining the lumen 536 of the sheath 530 between adjacent folds of the wall 535 of the sheath 530, it is to be appreciated that the spacing between folds is greatly augmented for illustrative purposes only. As shown in FIG. 7, the sheath 530 may be expanded or unfolded from a first, collapsed outer diameter $D_1$ to a second, expanded outer diameter $D_2$. In some embodiments, the first, collapsed diameter may be about 0.25 mm to about 0.5 mm (about 0.01 inches to about 0.02 inches) or about 0.355 mm to about 0.457 mm (about 0.014 inches to about 0.018 inches), and in some embodiments the second, expanded diameter may be 0.5 mm to about 2.0 mm (about 0.02 inches to about 0.08 inches) or about 0.75 mm to about 1.15 mm (about 0.03 inches to about 0.045 inches). For instance, in some embodiments the first, collapsed diameter $D_1$ may be about 0.355 mm to about 0.457 mm (about 0.014 inches to about 0.018 inches) and may open to a second, expanded diameter $D_2$ of about 0.75 mm to about 1.15 mm (about 0.03 inches to about 0.045 inches). Thus, in some embodiments, the sheath 530 may expand to 2 times or more, 2.5 times or more, or 3 times or more of its collapsed, folded diameter. Although some suitable dimensions are disclosed, one of skill in the art, incited by the present disclosure, would understand that desired dimensions may deviate from those expressly disclosed herein.

FIGS. 8A and 8B are cross-sectional views illustrating an alternative arrangement of expanding a sheath 630 of a perfusion guidewire 610. This cross-sectional view may be taken at a distal location proximate the distal end of the sheath 630. A seal 650 may be formed which partially or entirely seals the distal end of the sheath 630. The seal 650 may be, for example, an adhesive or weld (e.g., heat bonding) that adheres the inner wall of the sheath 630 to itself when the sheath 630 is in a collapsed configuration wrapped around the circumference of the elongate core member 620, as shown in FIG. 8A. The affinity of the seal 650 may be sufficiently strong such that pressure is allowed to build up in the lumen 636 of the sheath 630 prior to dissociation of adjacent layers of the wall 635 of the wrapped sheath 630. The elevated pressure within the lumen 636 of the sheath 630 achieved prior to breaching the seal 650 may help to enlarge a pathway crossing an occlusion within the vasculature of a patient in some instances. FIG. 8B illustrates the arrangement of the elongate core member 620 and the sheath 630 once the sheath 630 has been fully expanded. As shown in FIG. 8B, the seal 650 is shown secured to a portion of the inner surface 633 of the sheath 630. However, in other embodiments, the seal 650 may be configured to dissolve, disintegrate, or otherwise dissipate, and thus may not be visible when the sheath 630 is expanded.

Figure 9A:
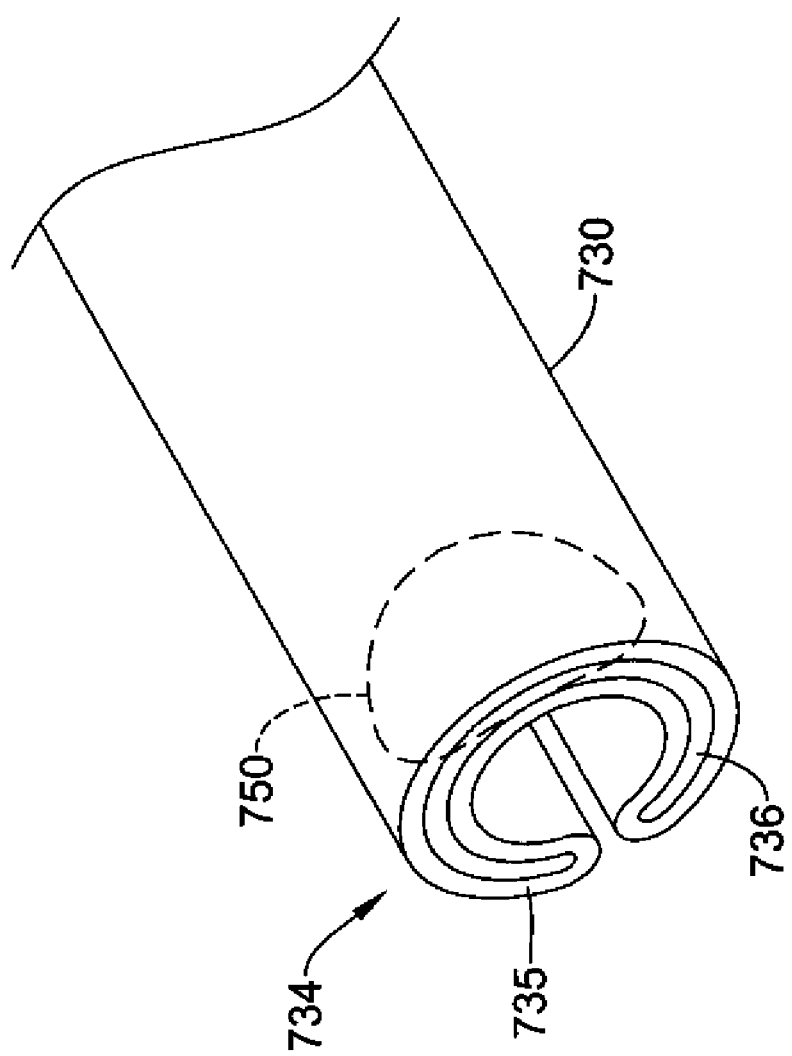
Figure 9B:
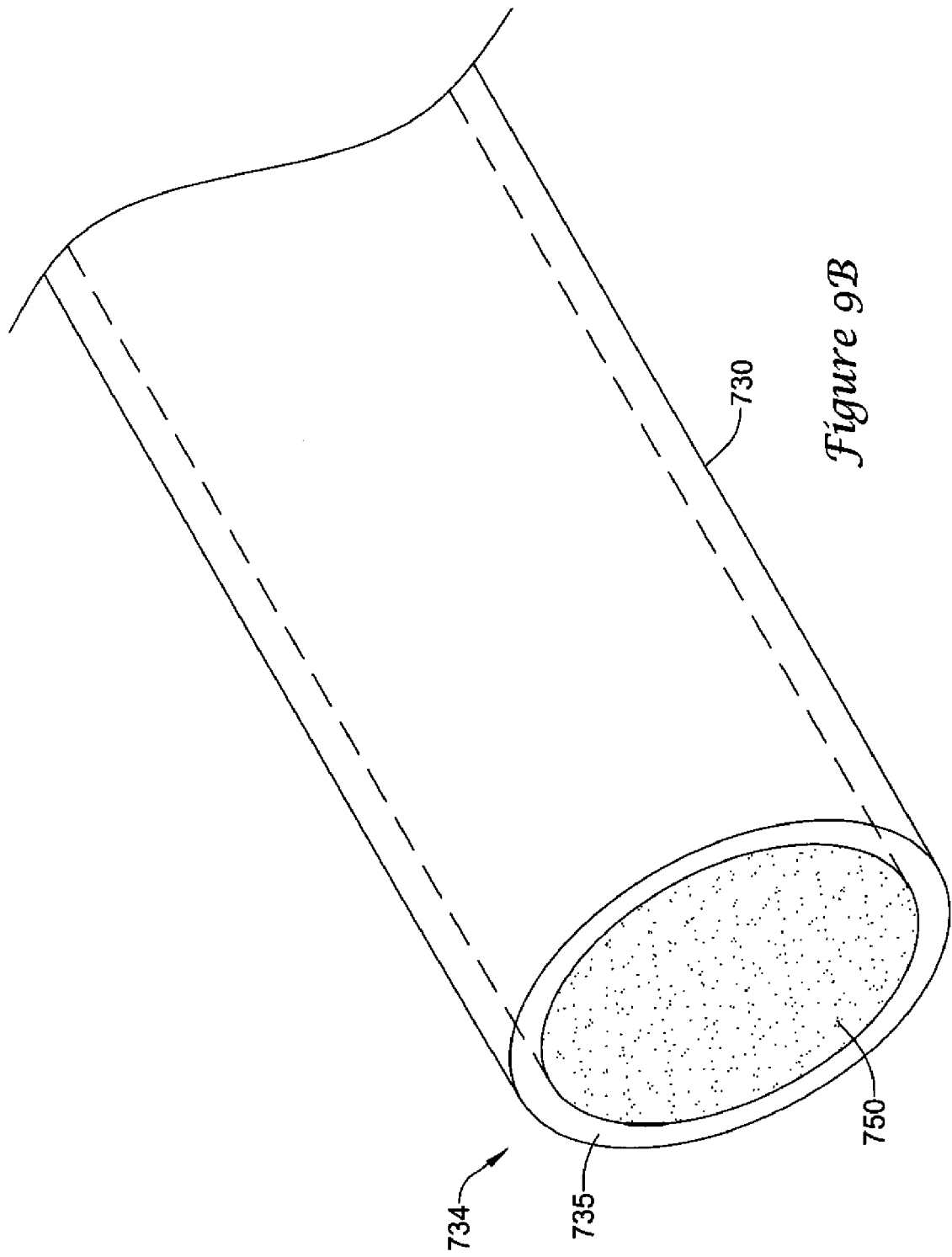

FIGS. 9A-9C illustrate an alternative arrangement of using a seal in the form of a flap 750 for the purpose of building up internal pressure within the lumen 736 of the sheath 730 in order to expand the sheath 730. It is noted that the elongate core member is not illustrated for purposes of clarity. Although FIG. 9A illustrates gaps defining the lumen 736 of the sheath 730 between adjacent folds of the wall 735 of the sheath 730, it is to be appreciated that the spacing between folds is greatly augmented for illustrative purposes only. The flap 750 may be attached to a distal portion of the sheath 730, such as the distal end 734 of the sheath 730 as shown in the illustrative embodiment. However, the flap 750 may be attached at another location as desired. FIG. 9A shows the flap 750 positioned in the collapsed lumen 736 of the sheath 730 tightly wrapped around the circumference of an elongate core member. As fluid pressure is initially applied through the lumen 736, the flap 750 prevents fluid from egressing out the distal end 734 of the sheath 730 prior to the internal pressure reaching a threshold level. Thus, the internal fluid pressure may expand the sheath 730 as shown in FIG. 9B. Once the internal fluid pressure reaches a threshold level, as shown in FIG. 9C, the flap 750 is released from the lumen 736, opening the lumen 736 to the distal end 734 of the sheath 730, allowing fluids to be perfused through the lumen 736 of the sheath 730. Thus, the flap 750 may partially or fully inhibit the flow of fluid through the lumen 736 of the sheath 730 at pressures below a desired threshold pressure.

Figure 10B:
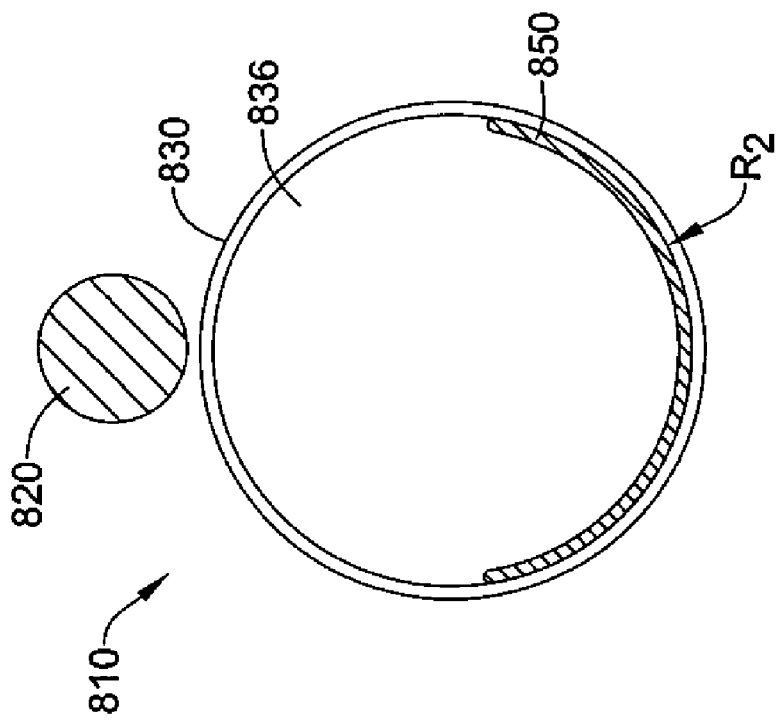
FIGS. 10A and 10B are cross-sectional views illustrating an alternative arrangement of expanding a sheath of a perfusion guidewire.
Figure 10A:
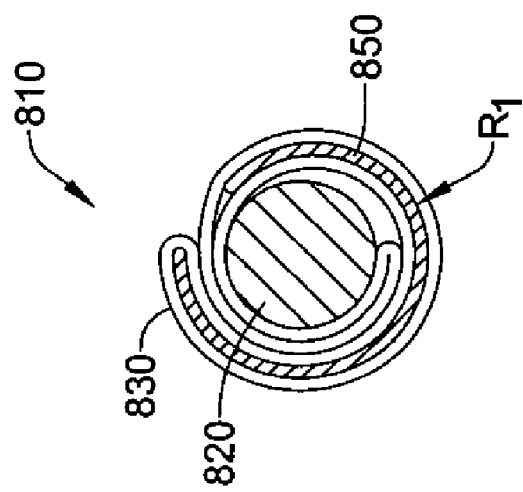

FIGS. 10A and 10B are cross-sectional views illustrating an alternative arrangement of expanding a sheath 830 of a perfusion guidewire 810. As shown in FIG. 10A, the sheath 830 may include a bi-stable member 850 which is predisposed to assume a first stable position, yet when sufficient force is applied, the bi-stable member 850 may be predisposed to assume a second stable position, as shown in FIG. 10B. For instance, the bi-stable member 850 may be an arcuate member assuming a first radius $R_1$ in a first configuration and assuming a second radius $R_2$, larger than the first radius $R_1$, in a second configuration. In such a case, the bi-stable member 850 may initially assume the first configuration, shown in FIG. 10A, thereby tightly wrapping the sheath 830 around the circumference of the elongate core member 820. When sufficient force, such as internal fluid pressure, is applied to the sheath and/or the bi-stable member 850 such that the bi-stable member 850 is urged beyond a threshold position, the bi-stable member 850 will then assume the second configuration, shown in FIG. 10B. In other embodiments, the bi-stable member 850 may be predisposed to assume any other position or shape.

In some embodiments, the bi-stable member 850 may be formed of a thermally responsive material, such as a shape memory polymer or a shape memory alloy, which is transformable between a first shape and a second shape as a result of being subjected to heating above a predetermined transition temperature. In some embodiments, the predetermined transition temperature may be chosen to be at or just below the body temperature of a patient. In some embodiments, the predetermined transition temperature may be in the range of 70° F. to about 98° F., in the range of 80° F. to about 95° F., in the range of about 90° F. to about 95° F., or another desired temperature. In other words, the bi-stable member 850 may assume a first shape at temperatures below the predetermined transition temperature, and may assume a second shape at temperatures above the predetermined transition temperature. In embodiments wherein the predetermined transition temperature is chosen to be at or below the body temperature of a patient, the bi-stable member 850 may assume a first, small radius configuration (holding the sheath in a tightly wrapped configuration around the circumference of the elongate core member 820) external of the body of the patient, but may transition to a second, larger radius configuration (unwrapping the sheath 850 in order to open the lumen 836 of the sheath 830) upon reaching the predetermined transition temperature within the body of the patient. One of skill in the art would understand other materials, configurations, and/or stimuli sufficient for actuating the sheath 830 between a first, collapsed configuration and a second, expanded configuration.

Figure 11A:
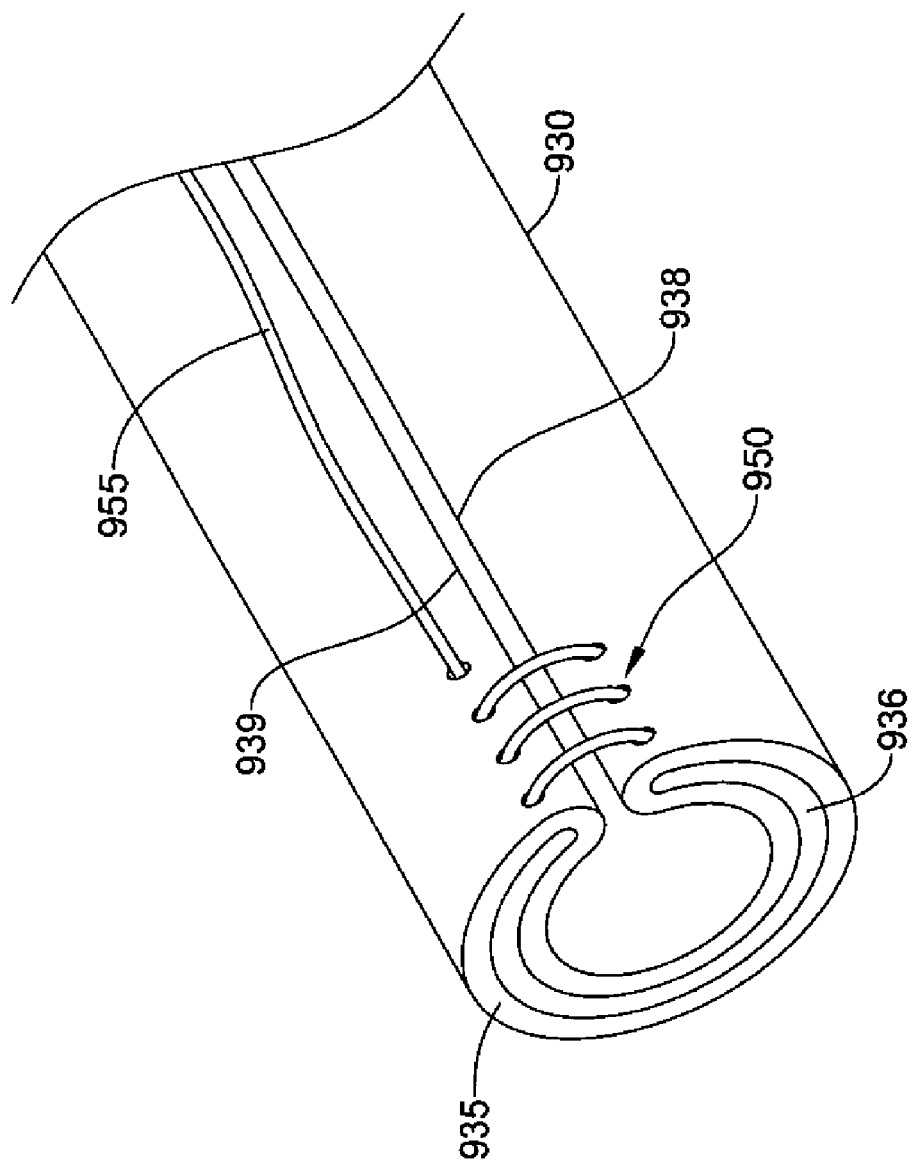
FIG. 11A illustrates yet a further embodiment of a sheath restrained with a suture in a collapsed configuration for insertion within the vasculature of a patient.
Figure 11B:
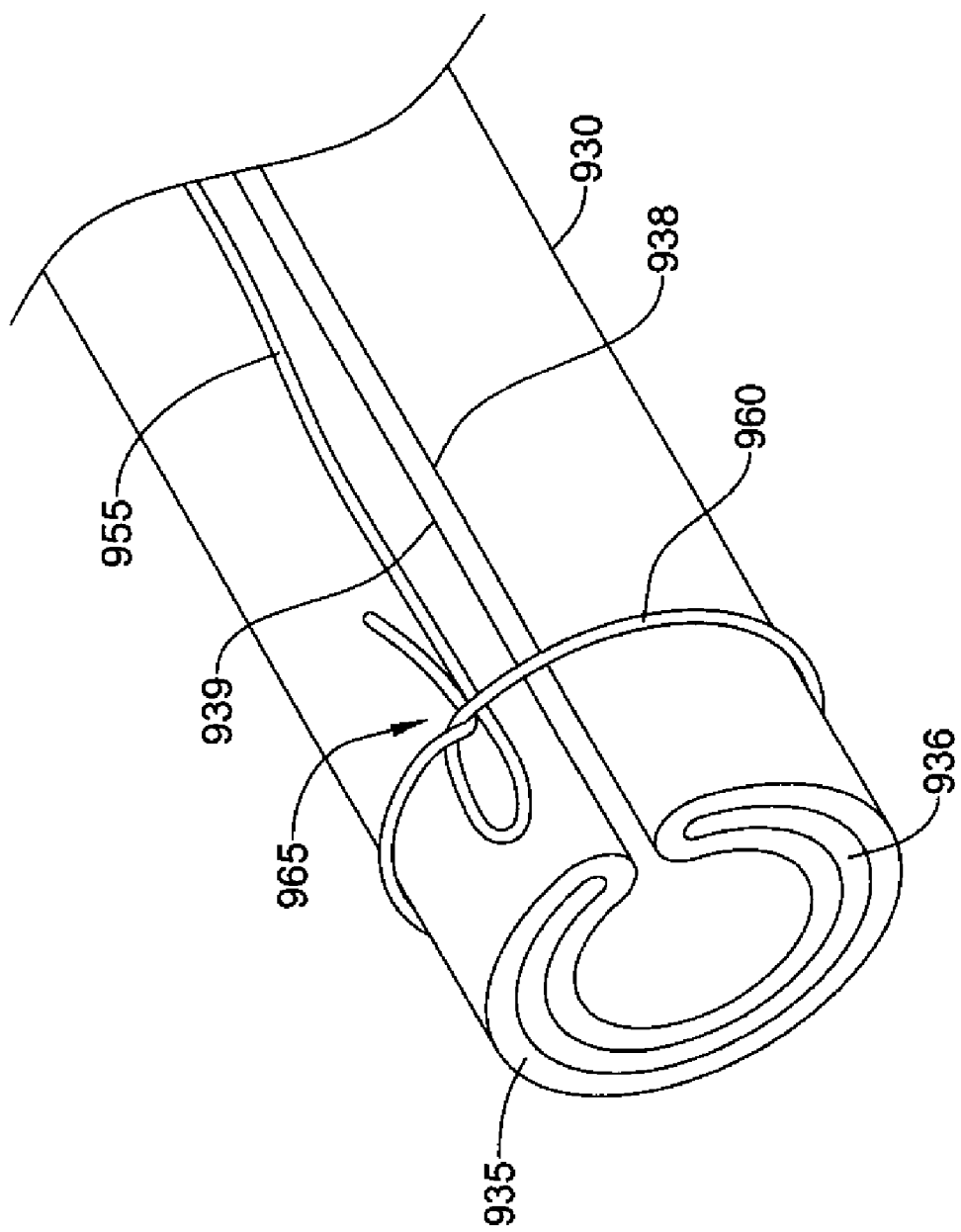
FIG. 11B illustrates another embodiment of a sheath restrained with a filament in a collapsed configuration for insertion within the vasculature of a patient.

FIGS. 11A and 11B illustrate yet further embodiments of a sheath 930 restrained in a collapsed configuration for insertion within the vasculature of a patient. It is noted that the elongate core member is not illustrated in FIGS. 11A and 11B for purposes of clarity. Although FIGS. 11A and 11B illustrate gaps defining the lumen 936 of the sheath 930 between adjacent folds of the wall 935 of the sheath 930, it is to be appreciated that the spacing between folds is greatly augmented for illustrative purposes only. The sheath 930 is collapsed and folded, defining two longitudinal edges or creases 938, 939. The collapsed sheath 930 is rolled into an annular configuration around an elongate core member (not shown).

As shown in FIG. 11A, one or a plurality of strands or filaments such as one or more sutures 950 may be used to restrain the first longitudinal edge or crease 938 proximate the second longitudinal edge or crease 939, or other portion of the outer surface of the sheath 930, holding the sheath 930 in the collapsed annular configuration. A pull member 955 may be attached to or integral with the suture(s) 950. In some embodiments the suture(s) 950 and the pull member 955 may be monolithic, or the suture(s) 950 may be secured to, adhered to, or otherwise attached to the pull member 955. The pull member 955 may extend substantially the entire length of the sheath 930, thus may be accessible proximal of an incision, exterior of the body of the patient during a medical procedure. Therefore, actuation of the pull member 955 proximally may release the suture(s) 950, allowing the sheath 930 to expand when desired. In some embodiments, instead of extending exterior of the sheath 930, the pull member 955 may extend through the central passage formed by the sheath 930 in the collapsed annular configuration.

As shown in FIG. 11B, one or more strands or other filaments 960 may be formed into one or more loops which encircle the sheath 930 to hold the sheath 930 in the collapsed annular configuration. In some embodiments the strand(s) or filament(s) 960 and the pull member 955 may be monolithic, or the strand(s) or filament(s) 960 may be secured to, adhered to, or otherwise attached to the pull member 955. The one or more strands or other filaments 960 may be selectively released by retraction of the pull member 955 proximally such that the sheath 930 is allowed to expand. The strand(s) or filament(s) 960 may be formed into a knot 965, such as a "slip knot" or other type of releasable knot or interlacement, which may securely hold the sheath 930 in the collapsed annular configuration until the pull member 955 is retracted proximally. In some embodiments, the free end of the strand(s) or filament(s) 960 may be secured to the sheath 930, or in other embodiments, the free end of the strand(s) or filament(s) 960 may be loose from the sheath 930 such that upon expanding the sheath 930 (e.g., releasing or untying the knot 965) the strand(s) or filament(s) 960 and/or the pull member 955 may be removed from the vasculature. In some embodiments, instead of extending exterior of the sheath 930, the pull member 955 may extend through the central passage formed by the sheath 930 in the collapsed annular configuration.

Other means may be utilized in order to restrain the first longitudinal edge or crease 938 proximate the second longitudinal edge or crease 939, or other portion of the outer surface of the sheath 930. For instance, the first longitudinal edge or crease 938 may be adhesively bonded, thermally welded (e.g., laser welding, RF welding), or otherwise temporarily secured to another portion of the outer surface of the sheath 930, such as the second longitudinal edge or crease 939, restraining the sheath 930 in the collapsed configuration. The temporary bond may be broken by providing sufficient force (e.g., applied pressure, mechanical urging) to the bonded region, thereafter allowing the sheath to expand.

Figure 12:
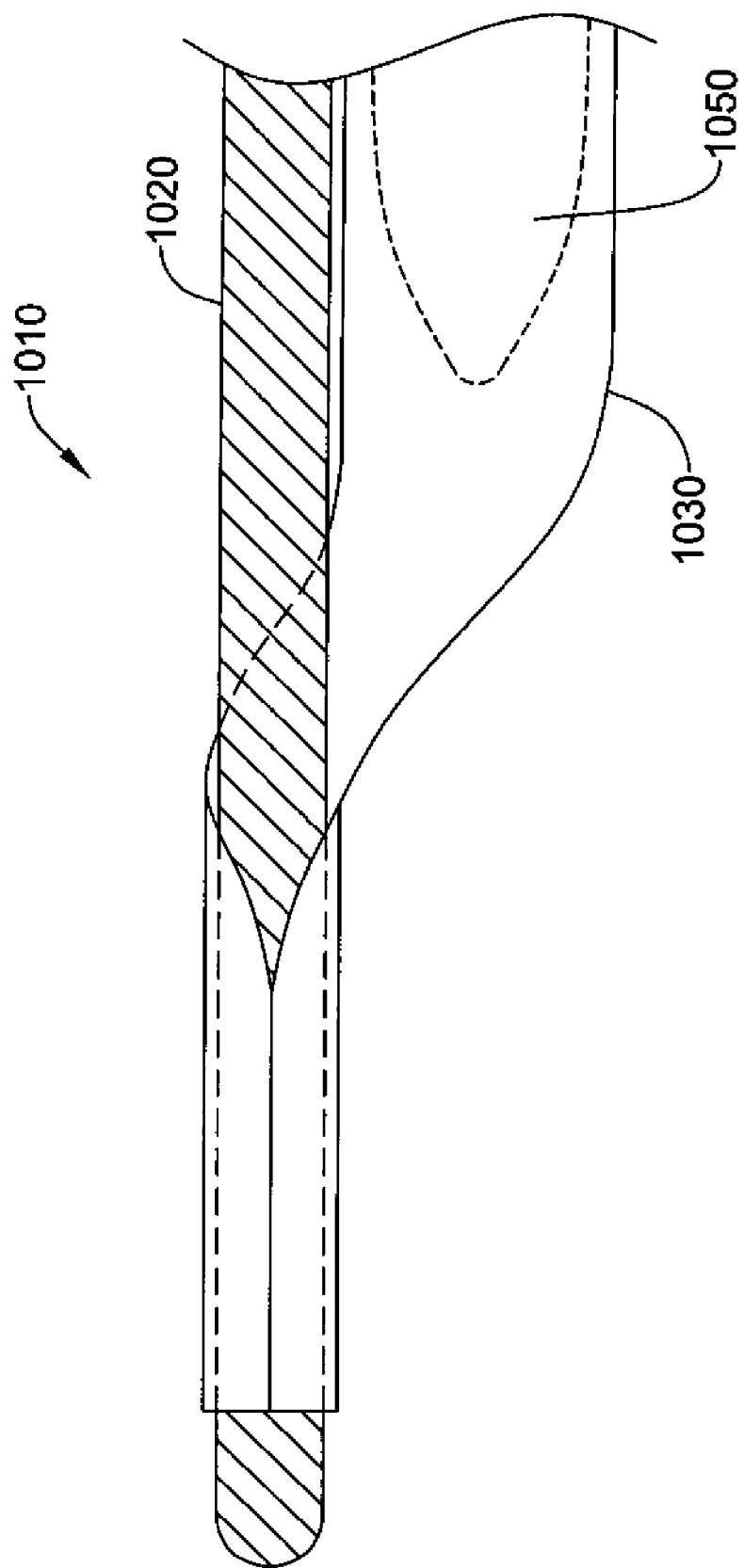
FIG. 12 illustrates a further embodiment of an alternative arrangement of expanding a sheath of a perfusion guidewire.

FIG. 12 illustrates another embodiment of a perfusion guidewire 1010 including an elongate core member 1020 and a sheath 1030 wrapped around the circumference of a distal portion of the elongate core member 1020. A dilator 1050 may be inserted through the lumen of the sheath 1030 and advanced distally. The dilator 1050 urges the sheath 1030 to be unfolded and expanded from the folded, wrapped configuration to the expanded configuration of the sheath 1030. As the sheath 1030 is unwrapped and expanded, the sheath 1030 is dissociated from the elongate core member 1020 such that the elongate core member 1020 may extend alongside and generally parallel with the sheath 1030.

Figure 13A:
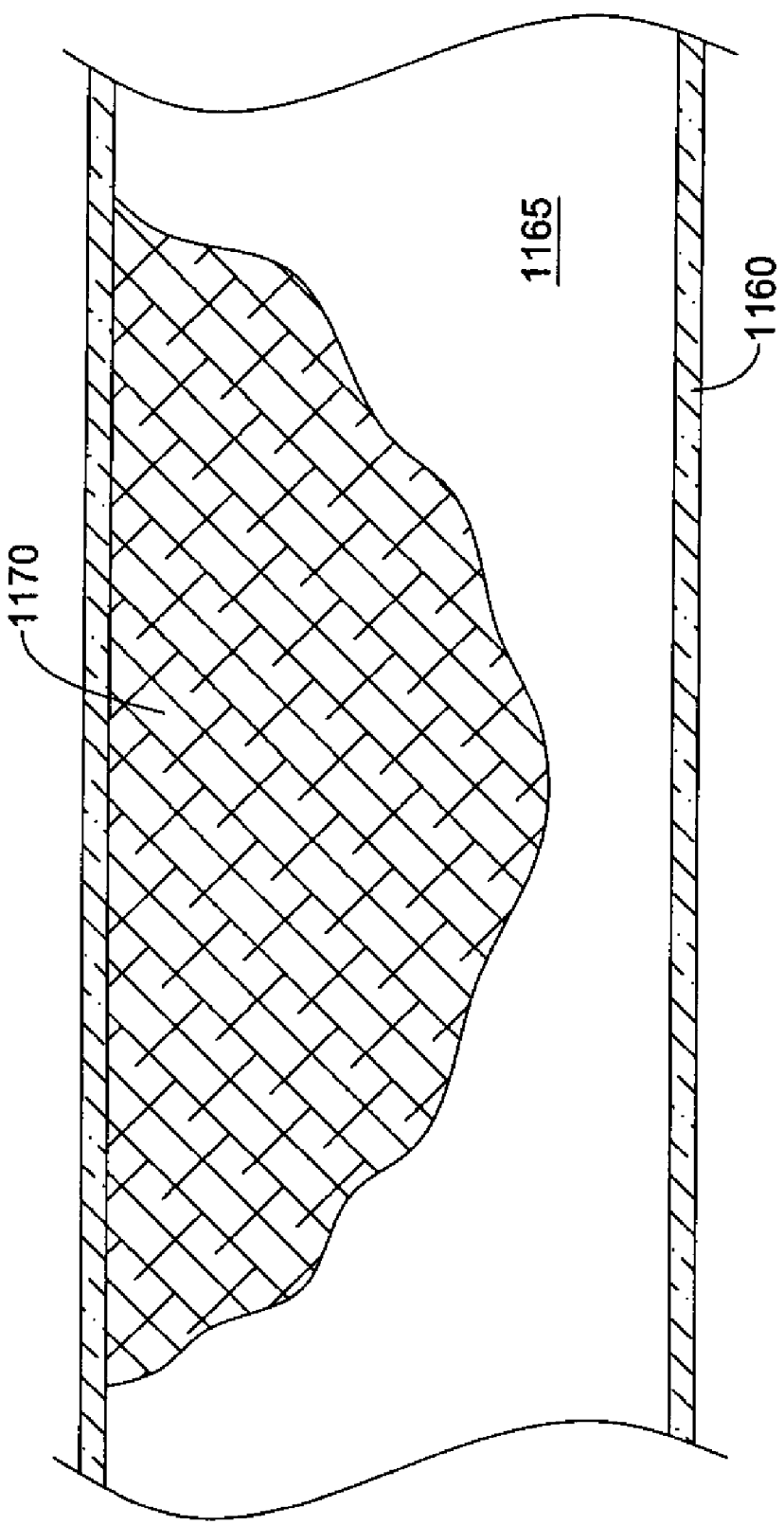

An exemplary method of using the illustrative perfusion guidewire 10 is depicted in FIGS. 13A-13F. FIG. 13A illustrates an occlusion 1170, which may be, for example, a thrombus or thromboembolus, obstructing the lumen 1165 of a vessel 1160. The occlusion 1170 may partially or entirely inhibit the flow of blood through the vessel 1160, causing medical complications to the patient.

Figure 13B:
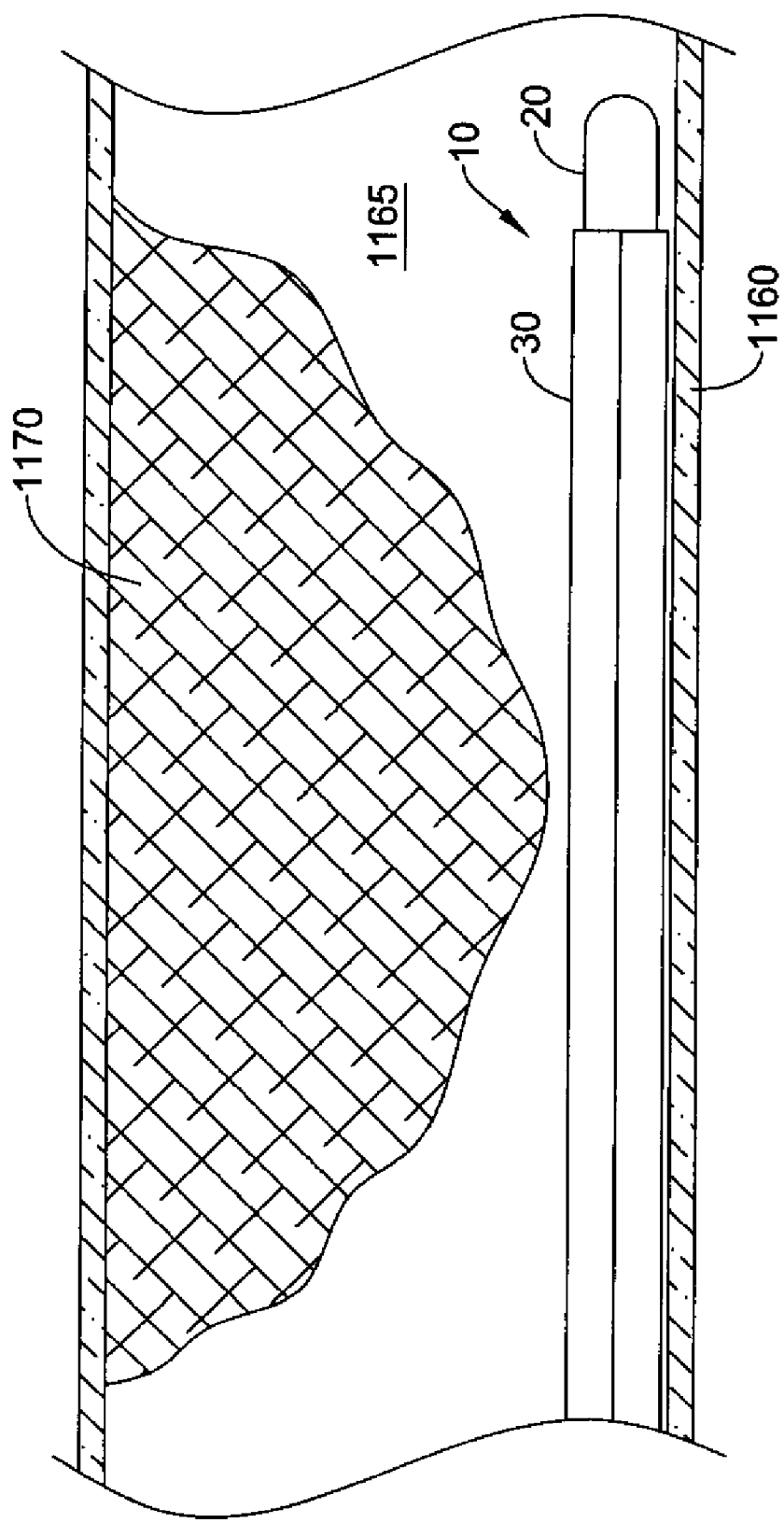

During a medical procedure, the perfusion guidewire 10, having the sheath 30 tightly folded and wrapped around the circumference of the elongate core member 20, may be advanced through the vasculature through the vessel 1160 to a location proximate the occlusion 1170, as shown in FIG. 13B. The sheath 30 may be releasably secured to the elongate core member 20 such that longitudinal movement of the elongate core member 20 corresponds to equivalent longitudinal movement of the sheath 30. The low profile of the perfusion guidewire 10 in the collapsed configuration allows the perfusion guidewire 10 to be advanced distal of the occlusion 1170 without dislodging or otherwise adversely disturbing the occlusion 1170.

Figure 13C:
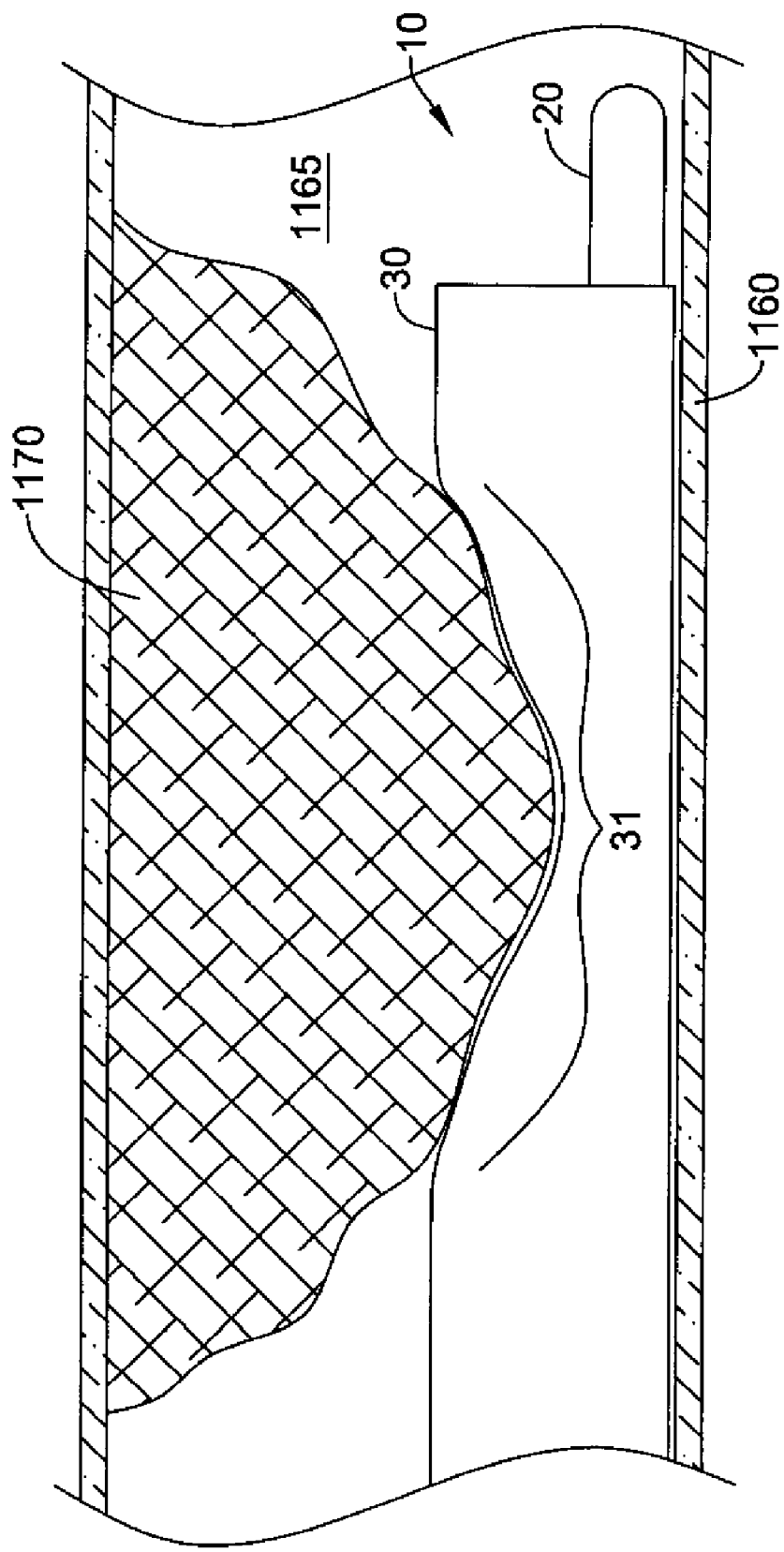

Once positioned across the occlusion 1170, the sheath 30 may be expanded to a larger diameter, as shown in FIG. 13C. For example, fluid pressure may be administered through the lumen 36 of the sheath 30 from a pressure device coupled to the connector 40 at the proximal end 32 of the sheath 30 proximal of an incision and external of the body of the patient. As shown in the FIGS., the sheath 30 may be expanded to 2 times or more, 2.5 times or more, or 3 times or more of its initial collapsed diameter. In other embodiments, the sheath 30 may be expanded by other means as described herein. For example, a bi-stable member or a dilator may be used to expand the sheath 30, or an outer sheath or suture, restraining the sheath 30 in the collapsed configuration, may be removed, thereby releasing the sheath 30 to be expanded. One of skill in the art, incited by the present disclosure, would understand additional equivalent means of expanding the sheath 30 once properly positioned across the occlusion 1170.

In some embodiments, such as that shown, when expanded, the occlusion 1170 may restrict full expansion of the sheath 30 along a portion of the sheath 30. The constricted portion 31 of the sheath 30 may conform to the contour of the occlusion 1170 within the vessel 1160. However, in other embodiments the sheath 30 may more fully expand through the region of the occlusion 1170, thus radially compressing the occlusion 1170 against the wall of the vessel 1160.

Once positioned and expanded, the sheath 30 may be used to perfuse a perfusate, such as oxygenated blood or a medicinal fluid, to a location distal of the occlusion 1170. The perfusate may be administered through the lumen 36 of the sheath 30 from a pressure device coupled to the connector 40 at the proximal end 32 of the sheath 30 proximal of an incision and external of the body of the patient. Therefore, the sheath 30 may provide perfusate to tissue distal of the occlusion 1170. Even in embodiments in which the sheath 30 retains a restriction attributable to the constricted portion 31 conforming to the contour of the occlusion 1170, the sheath 30 may allow a sufficient quantity of perfusate to reach tissue distal of the occlusion 1170.

Once expanded, the sheath 30 may be released from the elongate core member 20 such that the elongate core member 20 may be translated independent of the sheath 30. In the illustrated embodiment, the elongate core member 20 is positioned within the lumen 36 of the sheath 30. However, as described herein, in other embodiments, the elongate core member 20, once released from the sheath 30 may be positioned generally parallel to and alongside the exterior of the sheath 30. In embodiments wherein the elongate core member 20 is positioned within the lumen 36 of the sheath 30, the elongate core member 20 may be withdrawn from the lumen 36 or retained in the lumen 36 during perfusion of a perfustate through the lumen 36, as desired.

Figure 13D:
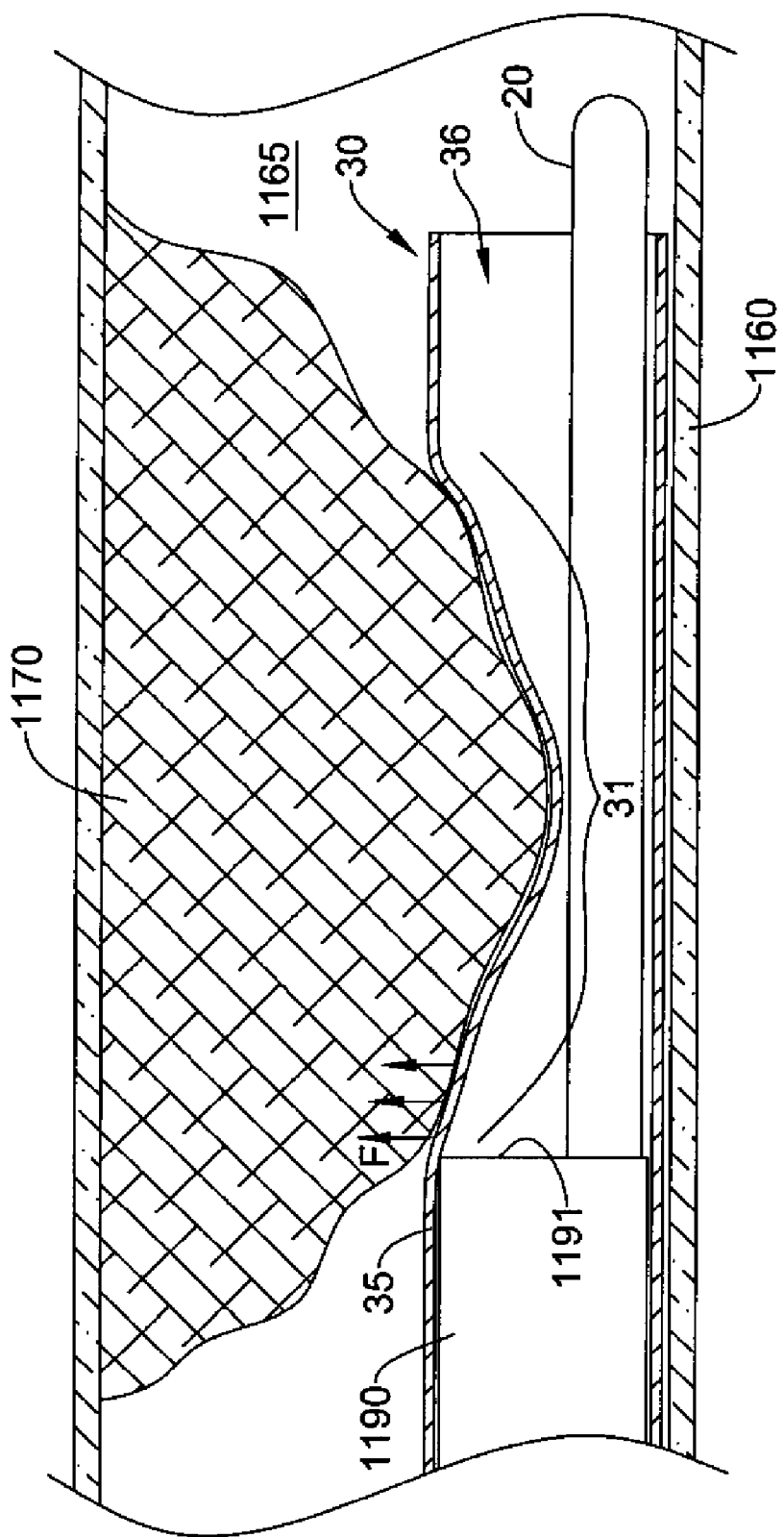

As shown in FIG. 13D, once the sheath 30 has been expanded and released from the elongate core member 20, the elongate core member 20 may be used to track additional medical devices, such as an embolus extractor, a distal protection device, a balloon catheter, a stent placement catheter, an embolic coil placement device, or the like, through the vasculature to a location proximate the occlusion 1170. A medical device 1190, illustrated as a catheter, may be advanced over the elongate core member 20 through the lumen 36 of the sheath 30. As the medical device 1190 approaches the occlusion 1170, the sheath 30 may act as a "shoehorn" for the medical device 1190. That is, the sheath 30 may facilitate passage of the medical device 1190 distally past the occlusion 1170 without adversely affecting the occlusion 1170 (e.g., dislodging and/or subjecting the occlusion 1170 to shear stresses). As the medical device 1190 approaches the constricted portion 31 of the sheath 30, resultant of the sheath's 30 conformity around the occlusion 1170, the leading edge 1191 of the medical device 1190 may engage the wall 35 of the sheath 30. As the medical device 1190 is urged further distally, the leading edge 1191 of the medical device 1190 urges the wall 35 radially outward, subjecting radially compressive forces F upon the occlusion 1170. Unlike circumstances in which the sheath 30 is not initially positioned across the occlusion 1170 prior to advancing a medical device 1190 distal of the occlusion 1170, the occlusion 1170 experiences minimal axial or shear stresses as the medical device 1190 is advanced past the occlusion 1170. This is realized in that the axial displacement of the medical device 1190 is translated into radial forces to the occlusion 1170 by the "shoehorn" effect of the sheath 30. In circumstances in which the medical device 1190 is advanced past the occlusion 1170 without the aid of sheath 30, the longitudinal movement of the medical device 1190 may dislodge the occlusion 1170, pushing it further distally in the vessel 1160, or subject the occlusion 1170 to undesirable levels of shear stresses.

Figure 13E:
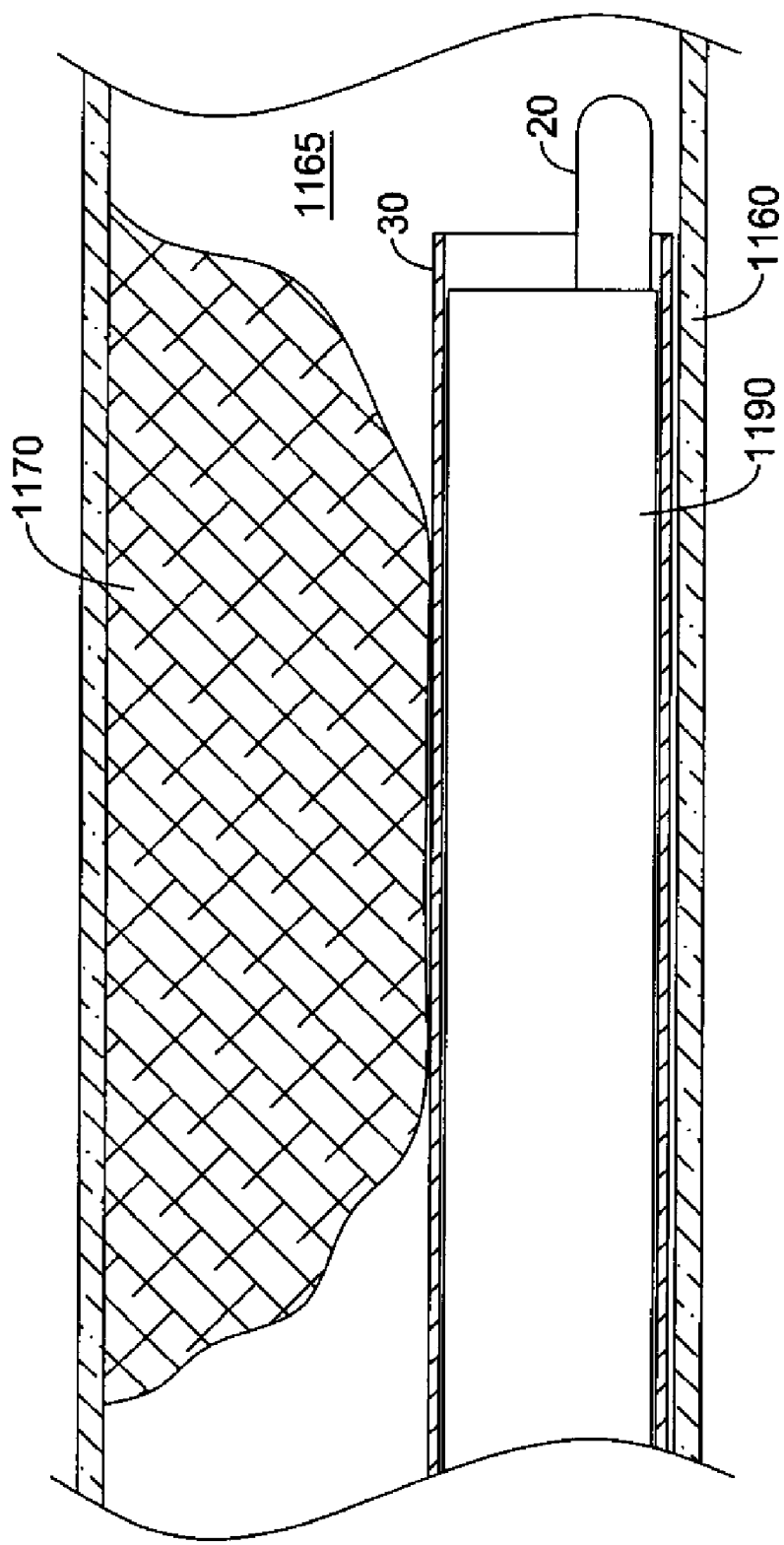

FIG. 13E illustrates the medical device 1190 extending through the sheath 30 to a location distal of the occlusion 1170. The occlusion 1170 is shown radially compressed toward the wall of the vessel 1160, yielding to the enlargement of the sheath 30 as the medical device 1190 is passed therethrough. With the medical device 1190 positioned distal of the occlusion 1170, a further medical procedure may be performed in order to provide treatment, remove the occlusion 1170, or the like. In some instances, once the medical device 1190 has been positioned across the occlusion 1170, the sheath 30 may be withdrawn from the vessel 1160, as shown in FIG. 13F, providing accessibility to the occlusion 1170 to perform a medical treatment.

Figure 14:
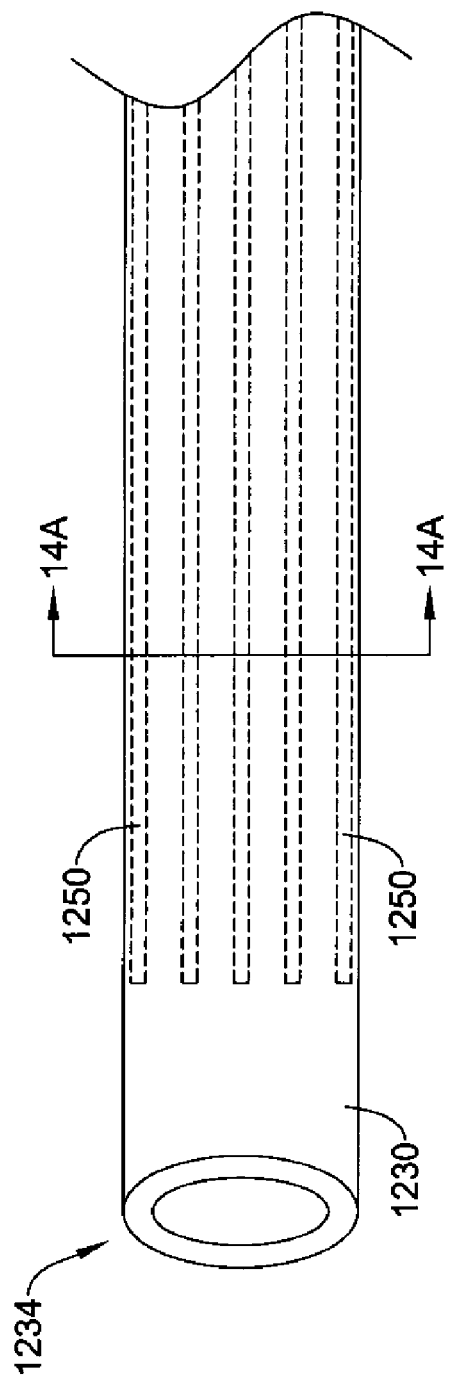
FIG. 14 illustrates a portion of another exemplary embodiment of a sheath for use in a perfusion guidewire.
Figure 14A:
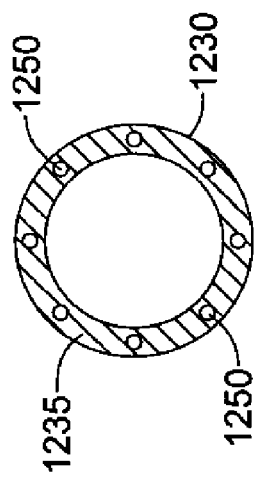
FIG. 14A is a cross-sectional view of the sheath of FIG. 14 taken along line 14A-14A of FIG. 14.

A portion of another illustrative embodiment of a sheath 1230 for use with a perfusion guidewire is depicted in FIG. 14. As shown in FIG. 14, a distal portion of the sheath 1230 proximate the distal end 1234 of the sheath 1230 may include a plurality of axial filaments 1250 extending along a length of the sheath 1230. In some embodiments, such as illustrated in FIG. 14A, the axial filaments 1250 may be embedded in the wall 1235 of the sheath 1230. However, in other embodiments, the axial filaments 1250 may be secured along either the inner or outer surface of the sheath 1230, if desired. In such instances, the axial filaments 1250 may be secured to the sheath 1230 by any suitable means, for example, solvent, heat or adhesive bonding. The axial orientation of the axial filaments 1250 provides the distal portion of the sheath 1230 with desired strength and rigidity, without compromising the ability of the sheath 1230 to be collapsed, folded and wrapped into a low profile around an elongate core member. The axial filaments 1250 may be formed of any suitable material. Some suitable materials include polymeric materials and metallic materials. Suitable polymeric materials include liquid crystal polymers, polyamide, polyester, polyvinylchloride, and polyethylene terephthalate, as well as other polymeric materials disclosed elsewhere herein, and the like. Suitable metallic materials include stainless steel, nickel-titanium alloys, tungsten, as well as other metallic materials disclosed elsewhere herein, and the like.

Figure 15A:
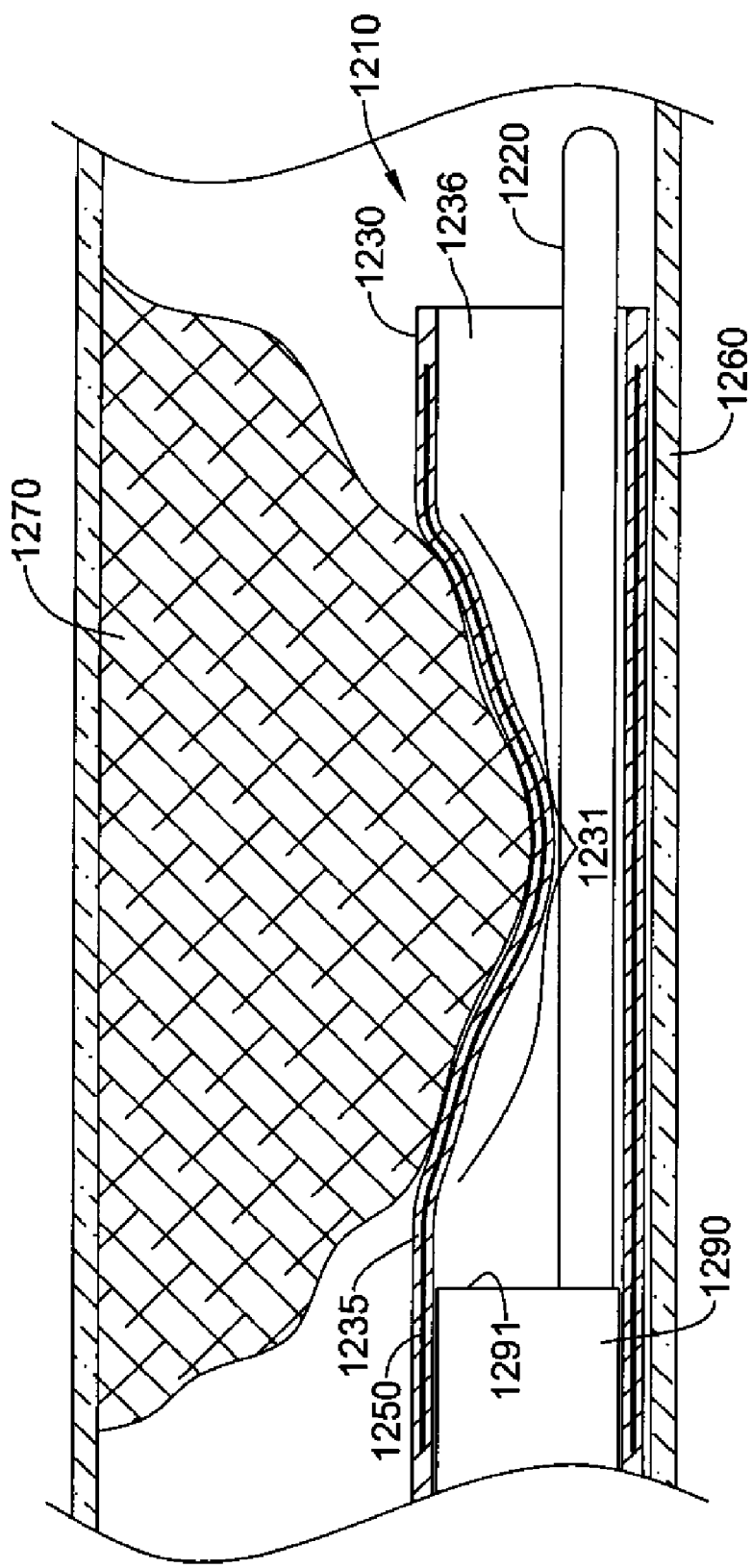
FIGS. 15A-15B illustrate an exemplary method of using the sheath of FIG. 14, in conjunction with an elongate core member, as a perfusion guidewire in a medical procedure.
Figure 15B:
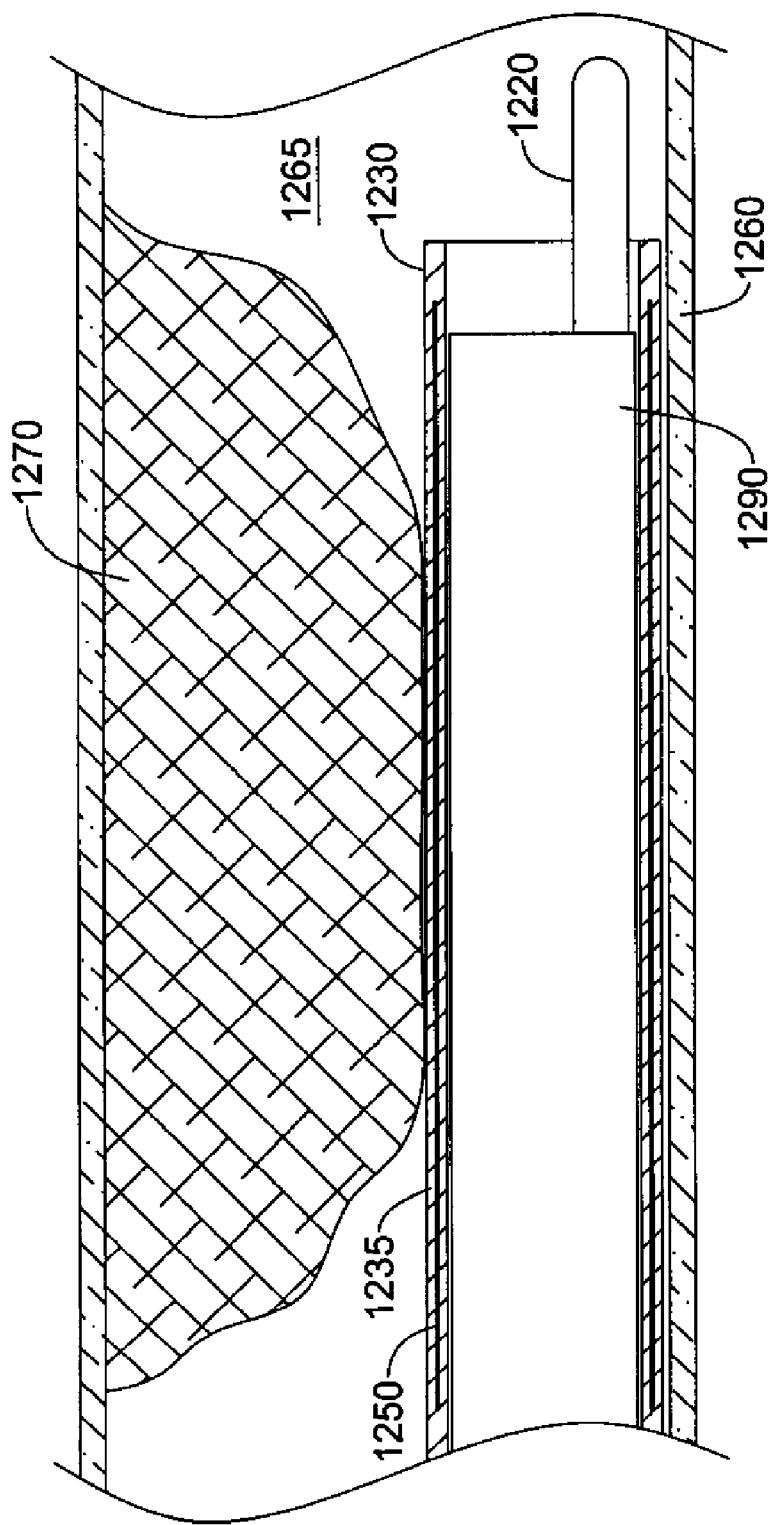

An exemplary method of using the illustrative sheath 1230 in conjunction with an elongate core member 1220, as a perfusion guidewire 1210, is depicted in FIGS. 15A-15B. The sheath 1230, as illustrated in FIG. 15A, has been expanded within the lumen 1265 of the vessel 1260 proximate an occlusion 1270. After initially being expanded, a constricted portion 1231 of the sheath 1230 may conform to the contour of the occlusion 1270 within the vessel 1260. The axial filaments 1250 may extend along the sheath 1230 through at least the constricted portion 1231 of the sheath 1230. The axial filaments 1250 may be sufficiently flexible such that the axial filaments 1250 may be readily curved through the constricted portion 1231 of the sheath 1230.

A medical device 1290, illustrated as a catheter, may be advanced through the lumen 1236 of the sheath 1230 to a location proximate the occlusion 1270. As the medical device 1290 approaches the occlusion 1270, the sheath 1230 may act as a "shoehorn" for the medical device 1290. That is, the sheath 1230 may facilitate passage of the medical device 1290 distally past the occlusion 1270 without adversely affecting the occlusion 1270 (e.g., dislodging and/or subjecting the occlusion 1270 to shear stresses). As the medical device 1290 approaches the constricted portion 1231 of the sheath 1230, resultant of the sheath's 1230 conformity around the occlusion 1270, the leading edge 1291 of the medical device 1290 may engage the wall 1235 of the sheath 1230. As the medical device 1290 is urged further distally, the leading edge 1291 of the medical device 1290 urges the wall 1235 radially outward, subjecting radially compressive forces upon the occlusion 1270. The axial filaments 1250 along the sheath 1230 may assist in radial compression of the occlusion 1270 and thus widening of the passage past the occlusion 1270, while guiding the medical device 1290 further distally through the lumen 1236.

FIG. 15B illustrates the medical device 1290 extending through the sheath 1230 to a location distal of the occlusion 1270. The occlusion 1270 is shown radially compressed toward the wall of the vessel 1260, yielding to the enlargement of the sheath 1230 as the medical device 1290 is passed therethrough. With the medical device 1290 positioned distal of the occlusion 1270, a further medical procedure may be performed in order to provide treatment, remove the occlusion 1270, or the like.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A perfusion guidewire for use in crossing an occlusion within a blood vessel of the body of a patient, the guidewire comprising:
    an elongate core member having a proximal portion, a distal portion and a longitudinal axis; and
    a collapsible sheath having a lumen therethrough, the sheath formed of a polymeric material, the sheath tightly wrapped around at least the distal portion of the elongate core member such that the wrapped sheath is folded upon itself, forming a plurality of layers of material in a radial direction from the longitudinal axis of the elongate core member, wherein the wrapped sheath is expandable to a larger diameter upon the introduction of pressurized fluid through the lumen such that the elongate core member is detached from and exterior to the sheath;
    wherein the wrapped sheath is wrapped about the elongate core member such that the wrapped sheath and elongate core member travel as a unit during navigation within the blood vessel of the body of the patient; and
    wherein the proximal portion of the elongate core member is positioned exterior to the lumen of the collapsible sheath and extends alongside the sheath.

2. The guidewire of claim 1, wherein the collapsible sheath is releasably affixed to the elongate core member.

3. The guidewire of claim 1, wherein the proximal portion of the elongate core member is positioned generally parallel to the collapsible sheath.

4. The guidewire of claim 1, wherein the sheath is formed of a generally nondistensible material.

5. The guidewire of claim 1, wherein the elongate core member is a solid member.

6. The guidewire of claim 1, wherein the elongate core member is a hollow member.

7. A perfusion guidewire for crossing an occlusion within a blood vessel of a patient, the guidewire comprising:
    an elongate core member having a distal portion, a proximal portion and an outer surface;
    a collapsible sheath having a first collapsed stated and a second expanded state, the collapsible sheath folded around at least the distal portion of the elongate core member in the collapsed state, the collapsible sheath including a wall having an outer surface and an inner surface defining a lumen, wherein the wall of the sheath is folded upon itself and against the outer surface of the elongate core member in the collapsed state, the collapsible sheath is expandable to the expanded state wherein the outer surface of the elongate core member is exterior to and extends alongside the sheath such that the elongate core member is detached from the sheath when the sheath is in the expanded state; and
    a luer fitting attached to the proximal end of the collapsible sheath, such that a proximal end of the lumen of the collapsible sheath is in fluid communication with another medical device exterior to the patient;
    wherein the collapsible sheath is releasably secured to the elongate core member in the collapsed state such that longitudinal movement of the elongate core member corresponds to equivalent longitudinal movement of the collapsible sheath.

8. The guidewire of claim 7, wherein in the collapsed state the collapsible sheath has a radial extent and in the expanded state the collapsible sheath has a radial extent at least two times the radial extent in the collapsed state.

9. The guidewire of claim 7, wherein the elongate core member extends along the outer surface of the collapsible sheath.

10. A perfusion guidewire for use in crossing an occlusion within a blood vessel of a body of a patient, the guidewire comprising:
    an elongate core member having a distal portion, a proximal portion, and a longitudinal axis;
    a sheath having a proximal end and a distal end, the sheath being convertible between a collapsed state and an expanded state, the sheath formed of a supple, yet generally nondistensible material, wherein in the collapsed state the sheath is wrapped around the elongate core member in a manner such that the sheath and elongate core member travel as a unit during navigation within the blood vessel of the body of the patient; and
    a luer fitting attached to the proximal end of the sheath, wherein during use the luer fitting attached to the proximal end of the sheath remains external of the body of the patient;
    wherein the proximal portion of the elongate core member is positioned exterior to the lumen of the collapsible sheath and extends alongside the sheath; and
    wherein in the expanded state the sheath is unattached to the elongate core member.

11. The guidewire of claim 10, wherein the wall of the sheath is folded upon itself in a serpentine arrangement.

12. The guidewire of claim 10, wherein the proximal portion of the elongate core member is positioned generally parallel to the sheath.

13. The guidewire of claim 10, wherein the sheath is releasably secured to the elongate core member in the collapsed state such that longitudinal movement of the elongate core member corresponds to equivalent longitudinal movement of the sheath.

14. The guidewire of claim 10, wherein the sheath includes an annular wall having a thickness of 0.002 inches or less.

15. The guidewire of claim 10, wherein the sheath includes an annular wall having a thickness of 0.001 inches or less.

* * * * *

UNITED STATES PATENT AND TRADEMARK OFFICE
CERTIFICATE OF CORRECTION

Page 1 of 1

Figure 4C:
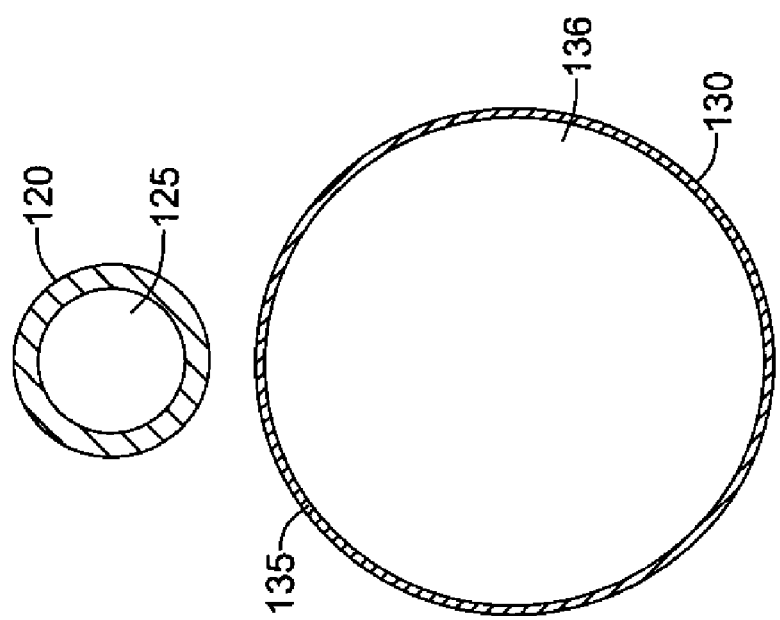
FIG. 4C is an alternative embodiment of a cross-sectional view of the perfusion guidewire of FIG. 4 in an expanded state.

PATENT NO. : 7,780,630 B2
APPLICATION NO. : 11/693795
DATED : August 24, 2010
INVENTOR(S) : Mark L. Jenson and William J. Drasler It is certified that error appears in the above-identified patent and that said Letters Patent is hereby corrected as shown below:

Column 9
Line 39: Before "As shown", insert -- FIG. 4C illustrates an alternative embodiment of the sheath 130 in an expanded configuration, wherein the elongate core member 120 may be a hollow member having an annular cross-section defining a lumen 125. --.

Line 39: Delete "FIG. 4B" and insert therefor -- FIGS. 4B and 4C --.

Signed and Sealed this
Twenty-second Day of March, 2011

David J. Kappos
*Director of the United States Patent and Trademark Office*